(12) United States Patent
Dupont et al.

(10) Patent No.: US 8,778,340 B2
(45) Date of Patent: Jul. 15, 2014

(54) ANTI-ANGIOGENESIS THERAPY FOR THE TREATMENT OF OVARIAN CANCER

(75) Inventors: Jakob Dupont, Hillsborough, CA (US); Cornelia Irl, Basel (CH)

(73) Assignee: Genentech, Inc., So. San Francisco, CA (US)

( * ) Notice: Subject to any disclaimer, the term of this patent is extended or adjusted under 35 U.S.C. 154(b) by 238 days.

(21) Appl. No.: 13/032,532

(22) Filed: Feb. 22, 2011

(65) Prior Publication Data

US 2011/0206662 A1  Aug. 25, 2011

Related U.S. Application Data

(60) Provisional application No. 61/439,819, filed on Feb. 4, 2011, provisional application No. 61/360,059, filed on Jun. 30, 2010, provisional application No. 61/351,231, filed on Jun. 3, 2010, provisional application No. 61/307,095, filed on Feb. 23, 2010.

(51) Int. Cl.
*A61K 39/395* (2006.01)

(52) U.S. Cl.
USPC .................................... 424/138.1; 424/155.1

(58) Field of Classification Search
None
See application file for complete search history.

(56) References Cited

U.S. PATENT DOCUMENTS

| | | | |
|---|---|---|---|
| 6,054,297 A | 4/2000 | Carter et al. | |
| 6,582,959 B2 | 6/2003 | Kim | |
| 6,703,020 B1 | 3/2004 | Thorpe et al. | |
| 6,884,879 B1 | 4/2005 | Baca et al. | |
| 7,060,269 B1 | 6/2006 | Baca et al. | |
| 2003/0190317 A1 | 10/2003 | Baca et al. | |
| 2003/0203409 A1 | 10/2003 | Kim | |
| 2003/0206899 A1 | 11/2003 | Ferrara et al. | |
| 2005/0112126 A1 | 5/2005 | Baca et al. | |
| 2005/0186208 A1 | 8/2005 | Fyfe et al. | |
| 2006/0093601 A1 | 5/2006 | Fong et al. | |

FOREIGN PATENT DOCUMENTS

| | | |
|---|---|---|
| EP | 0666868 B1 | 4/2002 |
| WO | 94/10202 | 5/1994 |
| WO | 96/30046 | 10/1996 |
| WO | 98/45332 | 10/1998 |
| WO | 2005/012359 A2 | 2/2005 |
| WO | 2005/044853 A2 | 5/2005 |
| WO | 2008/057562 A1 | 5/2008 |

OTHER PUBLICATIONS

Penson et al (J Clinical Oncology, Jan. 1, 2010, 28:154-159).*
Richardson et al (Gynecologic Oncology, 2008, 111:461-466).*
Micha et al (Int Journal Gynecol Cancer, 2007, 17:771-776).*
McMeekin et al (J Clinical Oncology, 2009, 27:15s, abstract 5540).*
Bast et al., "Chemotherapy: A new standard combination for recurrent ovarian cancer" Nat Rev Clin Oncol 7(10):559-560 (Oct. 2010).
Garcia et al., "Phase II Clinical Trial of Bevacizumab and Low-Dose Metronomic Oral Cyclophosphamide in Recurrent Ovarian Cancer: A Trail of the California, Chicago, and Princess Margaret Hospital Phase II Consortia" Journal of Clinical Oncology 26(1):76-82 (Jan. 1, 2008).
Aghajanian et al., "OCEANS: A Randomized, Double-Blind, Placebo-Controlled Phase III Trial of Chemotherapy with or without Bevacizumab in Patients with Platinum-Sensitive Recurrent Epithelial Ovarian, Primary Peritoneal, or Fallopian Tube Cancer" Journal of Clinical Oncology:1-7 (Apr. 23, 2012).
Burger et al., "Phase II trial of bevacizumab in persistent or recurrent epithelial ovarian cacer or primary peritoneal cancer: a Gynecologic Oncology Group study" J clin Oncol 25(33):5165-5171 ( 2007).
Stuart et al., "2010 Gynecologic Cancer InterGroup (GCIG) Consensus Statement on Clinical Trails in Ovarian Cancer" Int J of Gynecol Cancer 21(4):750-755 (May 2011).
U.S. Appl. No. 60/991,302, filed Nov. 30, 2007, Fuh et al.
Abstracts Presented for the Fortieth Annual Meeting of the Society of Gynecologic Oncologists; Gynecologic Oncology, Academic Press, London, GB, vol. 112, No. 2, pp. S2-S185 ( Feb. 1, 2009).
Alberts et al., "Improved therapeutic index of carboplatin plus cyclophosphamide versus cisplatin plus cyclophosphamide: Final Report by the Southwest Oncology Group of a Phase III randomized trial in stages III and IV ovarian cancer" J Clin. Oncol. 10(5):706-717 (May 1992).
Alvarez et al., "The prognostic significance of angiogenesis in epithelial ovarian carcinoma" Clin. Cancer Res. 5:587-591 (Mar. 1999).
Bast et al., "A radioimmunoassay using a monoclonal antibody to monitor the course of epithelial ovarian cancer" N Engl J Med 309(15):883-887 ( 1983).
Burger et al., "Phase III trial of bevacizumab (BEV) in the primary treatment of advanced epithelial ovarian cancer (EOC), primary peritoneal cancer (PPC), or fallopian tube cancer (FTC): A Gynecologic Oncology Group study" J. Clin. Oncol. (Abstract No. LBA1), 28:18s ( 2010).
Cannistra et al., "Phase II study of bevacizumab in patients with platinum resistant ovarian cancer or primary peritoneal serous cancer" J Clin Oncol 25(33):5180-5186 ( 2007).
International Search Report and Written Opinion for International Patent Application No. PCT/US2011/025651, 2011.
du Bois et al., "A randomized clinical trial of cisplatin/paclitaxel versus carboplatin/paclitaxel as first-line treatment of ovarian cancer" J Natl Cancer I 95(17):1320-1330 (Sep. 3, 2003).
Ferrara et al., "Clinical applications of angiogenic growth factors and their inhibitors" Nat Med 5(12):1359-1364 (Dec. 1999).
Folkman, "Tumor angiogenesis: Therapeutic implications" N Engl J Med 285:1182-1186 (Nov. 18, 1971).
Foster et al., "A review of the current evidence for maintenance therapy in ovarian cancer" Gynecologic Oncol. 115(2):290-301 (Nov. 1, 2009).

(Continued)

Primary Examiner — Laura B Goddard
(74) Attorney, Agent, or Firm — Janet M. Martineau

(57) ABSTRACT

This invention concerns in general treatment of diseases and pathological conditions with anti-VEGF antibodies. More specifically, the invention concerns the treatment of human patients susceptible to or diagnosed with cancer using an anti-VEGF antibody, preferably in combination with one or more additional anti-tumor therapeutic agents for the treatment of ovarian cancer.

10 Claims, 8 Drawing Sheets

(56) References Cited

OTHER PUBLICATIONS

Garcia et al., "Addition of bevacizumab to paclitaxel/carboplatin in first-line management of advanced ovarian cancer: Results of the GOG 0218 Phase III Study" Clin. Ovarian Cancer 3(2):E1-E5 (Nov. 2010).

Gasparini et al., "Prognostic and predictive value of tumour angiogenesis in ovarian carcinomas" Int. J. Cancer (Precl. Oncol.) 69:205-211 (1996).

Gasparini, G., "The rationale and future potential of angiogenesis inhibitors in neoplasia" Drugs 58:17-38 (1999).

Guppy and Rustin, "CA125 Response: can it replace the traditional response criteria in ovarian cancer?" Oncologists 7:437-443 (2002).

Han and Monk, "Bevacizumab in the treatment of ovarian cancer" Expert Review of Anticancer Therapy, Future Drugs Ltd., UK 7(10):1339-1345 (Oct 1, 2007).

Herzog et al., "Preliminary safety and efficacy results of a phase II study of oxaloplatin, docetaxel, and bevacizumab as first-line therapy of advanced cancer of the ovary, peritoneum, and fallopian tube" J. Clin. Oncol. (Abstract No. 5518), 25:18S (2007).

Hollingsworth et al., "Tumor angiogenesis in advanced stage ovarian carcinoma" Am. J. Pathol. 147(1):33-41 (Jul. 1995).

Houck et al., "The vascular endothelial growth factor family: Identification of a fourth molecular species and characterization of alternative splicing of RNA" Mol. Endocrin. 5:1806-1814 (1991).

Jemal et al., "Cancer Statistics, 2004" CA Cancer J Clin 54:8-29 (2004).

Kim et al., "Inhibition of vascular endothelial growth factor-induced angiogenesis suppresses tumour growth in vivo" Nature 362:841-844 (Apr. 1993).

Klagsbrun and D'Amore, "Regulators of angiogenesis" Ann Rev Physiol 53:217-239 (1991).

Leung et al. et al., "Vascular Endothelial Growth Factor is a Secreted Angiogenic Mitogen" Science 246:1306-1309 (Dec. 8, 1989).

Luo et al., "Differential inhibition of fluid accumulation and tumor growth in two mouse ascites tumors by an anti vascular endothelial growth factor/permeability factor neutralizing antibody" Cancer Res 58:2594-2600 (1998).

Mabuchi et al., "Maintenance treatment with bevacizumab prolongs survival in an in vivo ovarian cancer model" Clin. Cancer Res. 14(23):7781-7789 (Dec. 1, 2008).

Malonne et al., "Mechanisms of tumor angiogenesis and therapeutic implications: angiogenesis inhibitors" Clin. Exp. Metastas 17:1-14 (1999).

McGuire et al., "Cyclophosphamide and cisplatin compared with paclitaxel and cisplatin in patients with stage III and stage IV ovarian cancer" New Engl J Med 334:1-6 (1996).

McMeekin et al., "Phase II study of intravenous (IV) bevacizumab and paclitaxel intraperitoneal (IP) cisplatin, followed by bevacizumab consolidation for advanced ovarian (O) or peritoneal (P) cancers" J. Clin. Oncol. (Abstract No. 5540), 27:15s (2009).

Nakanishi et al., "The expression of vascular endothelial growth factor and transforming growth factor-beta associates with angiogenesis in epithelial ovarian cancer" Int J Gynecol Pathol 16(3):256-262 (Jul. 1997).

Ozols et al., "Phase III trial of carboplatin and paclitaxel compared with cisplatin and paclitaxel in patients with optimally resected stage III ovarian cancer: a gynecologic study" J Clin. Oncol. 21(17):3194-3200 (Sep. 1, 2003).

Paley et al., "Vascular endothelial growth factor expression in early stage ovarian carcinoma" Cancer 80( Suppl 98-106) (1997).

Penson et al., "Phase II study of carboplatin, paclitaxel, and bevacizumab with maintenance bevacizumab as first-line chemotherapy for advanced mullerian tumors" J. Clin. Oncol. 28(1):154-159 (Jan. 1, 2010).

Pfisterer et al., "Gemcitabine plus carboplatin compared with carboplatin in patients with platinum-sensitive recurrent ovarian cancer: an intergroup trial of the AGO-OVAR, the NCIC CTG, and the EORTC GCG" J. Clin. Oncol. 24:4699-4707 (2006).

Piccart et al., "Randomized intergroup trial of cisplatin-paclitaxel versus cisplatin-cyclophosphamide in women with advanced epithelial ovarian cancer: Three-Year Results" J Natl. Cancer I 92(9):699-708 (May 3, 2000).

Popkov et al., "Human/mouse cross-reactive anti-VEGF receptor 2 recombinant antibodies selected from an immune b9 allotype rabbit antibody library" J Immunol Methods 288:149-164 (May 2004).

Presta, L. G. et al., "Humanization of an Anti-Vascular Endothelial Growth Factor Monoclonal Antibody for the Therapy of Solid Tumors and Other Disorders" Cancer Res 57(20):4593-4599 (Oct. 15, 1997).

Reis-Filho and Tuft, "Triple negative tumours: a critical review" Histopathology 52:108-118 (Jan. 2008).

Richardson et al., "Combination gemcitabine, platinum, and bevacizumab for the treatment recurrent ovarian cancer" Gynecologic Oncol., Academic Press 111(3):461-466 (Dec. 1, 2008).

Roche: Avastin phase III study shows positive results in women with advanced ovarian cancer; Retrieved from the Internet: URL:http://www.roche.com/media/media_releases/med-cor-2010-02-25.htm.

Roche: Second phase III study showed Avastin-containing regimen helped women with cancer live longer without their disease getting worse; Retrieved from Internet: URL:http://www.roche.com/med-cor-2010-07-02, 2010.

Roche: Third phase III study of Avastin-based regimen met primary endpoint in ovarian cancer; Retrieved from the Internet: URL:http://www.roche.com/media/media_releases/med-cor-2011-02-08.htm, 2011.

Rose et al., "Preliminary results of a phase II study of oxaliplatin, docetaxel, and bevacizumab as first-line therapy of advanced cancer of the ovary, peritoneum, and fallopian tube" J. Clin. Oncol. (Abstract No. 5546), 27:15s (2009).

Rustin et al., "Re: new guidelines to evaluate the response to treatment in solid tumors (ovarian cancer)" J Natl. Cancer I 96(6):487-488 (Mar 17, 2004).

Rustin et al., "Use of CA-125 in clinical trial evaluation of new therapeutic drugs for ovarian cancer" Clin. Cancer Res. 10:3919-3926 (Jun. 1, 2004).

Rustin et al., "Use of CA-125 to define progression of ovarian cancer in patients with persistently elevated levels" J Clin. Oncol. 19(20):4054-4057 19(20):4054-4057 (Oct. 15, 2001).

Rustin, G., "Use of CA-125 to assess response to new agents in ovarian cancer trials" J. Clin. Oncol. 21(10s Suppl May 15 Supplement):187x-193x (2003).

Sato, "Molecular diagnosis of tumor angiogenesis and anti-angiogenic cancer therapy" Int J Clin Oncol 8(4):200-206 (Aug. 2003).

Streit et al., "Angiogenesis, lymphangiogenesis, and melanoma metastasis" Oncogene 22(20):3172-3179 (May 19, 2003).

Swenerton et al., "Cisplatin-cyclophosphamide versus carboplatin-cyclophosphamide in advanced ovarian cancer: a randomized phase III study of the National Cancer Institute of Canada Clinical Trials Group" J Clin. Oncol. 10(5):718-726 (May 1992).

Therasse et al., "New guidelines to evaluate the response to treatment in solid tumors" J Natl Cancer I 92(3):205-216 (2000).

Tonini et al., "Molecular basis of angiogenesis and cancer" Oncogene 22(42):6549-6556 (Sep. 29, 2003).

van Hinsbergh et al., "Angiogenesis and anti-angiogenesis: perspectives for the treatment of solid tumors" Ann Oncol 4( Suppl 4):60-63 (1999).

Yamamoto et al., "Expression of vascular endothelial growth factor (VEGF) in epithelial ovarian neoplasms: correlation with clinicopathology and patient survival, and analysis of serum VEGF levels" Br J Cancer 76:1221-1227 (1997).

Yoneda et al., "Expression of angiogenesis-related genes and progression of human ovarian carcinomas in nude mice" J Natl Cancer I 90(6):447-454 (Mar. 18, 1998).

"Second-Line Treatment Using Novel Chemotherapeutic and Biologic Agents" Japanese Journal of Cancer and Chemotherapy 36:730-735 (May 2009).

\* cited by examiner

Randomization (Cycle = 21 Days):

Arm I (Standard Chemotherapy)

Phase A  Chemotherapy * day 1 every 21 days x 6 cycles
Placebo (for bevacizumab) ** day 1 every 21 days beginning with cycle 2 x 5 cycles

Re-registration

Phase B  Placebo (for bevacizumab) ** day 1 every 21 days cycles 7 through 22

Arm II (Concurrent Bevacizumab)

Phase A  Chemotherapy * day 1 every 21 days x 6 cycles
bevacizumab ** day 1 every 21 days beginning with cycle 2 x 5 cycles

Re-registration

Phase B  Placebo (for bevacizumab) ** day 1 every 21 days cycles 7 through 22

Arm III (Extended Bevacizumab)

Phase A  Chemotherapy * day 1 every 21 days x 6 cycles
bevacizumab ** day 1 every 21 days beginning with cycle 2 x 5 cycles

Re-registration

Phase B  bevacizumab ** day 1 every 21 days cycles 7 through 22

*Paclitaxel 175mg/m² IV over 3 hours followed by Carboplatin AUC 6 IV over 30 minutes day 1 of cycles 1 through 6 only (Note: docetaxel 75mg/m² IV over 1 hour may be substituted for paclitaxel.)

**bevacizumab / Placebo 15mg/kg IV day 1 of each cycle beginning with cycle 2

FIG. 1

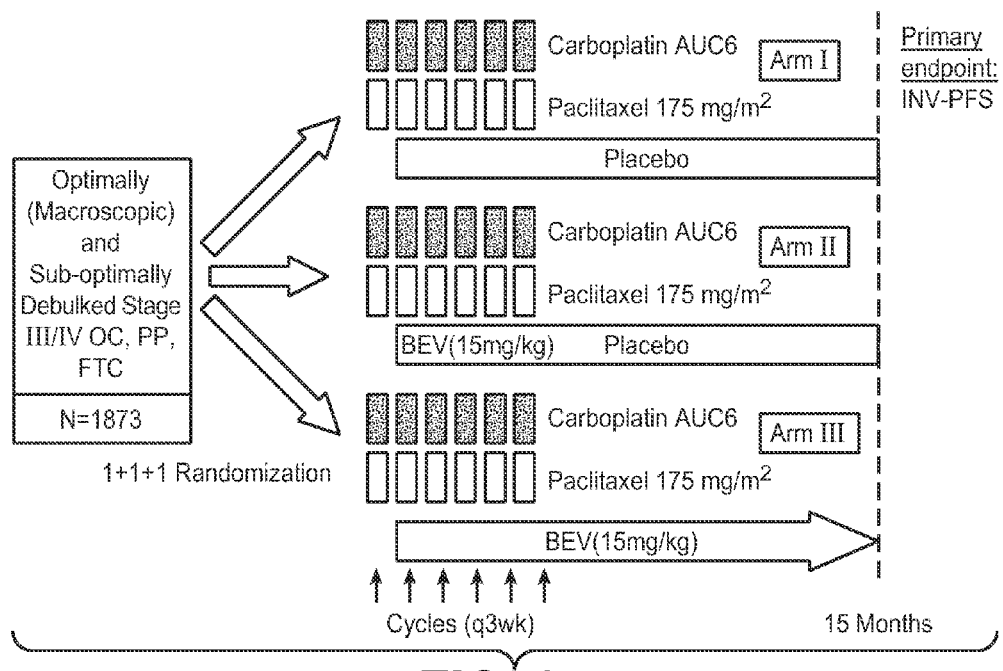

FIG. 2

Select Adverse Events
Onset Between Cycle 2 and 30 Days After Date of Last Treatment

| Adverse Event (Grade When Limited), n (%) | Arm I CP (n=601) | Arm II CP + BEV (n=607) | Arm III CP + BEV → BEV (n=608) |
|---|---|---|---|
| GI events[a] (grade ≥2) | 7 (1.2) | 17 (2.8) | 16 (2.6) |
| Hypertension (grade ≥3) | 10 (1.7)[b] | 36 (5.9)[b] | 63 (10.4)[b] |
| Proteinuria (grade ≥3) | 4 (0.7) | 4 (0.7) | 10 (1.6) |
| Pain (grade ≥3) | 55 (9.2)[b] | 73 (12.0)[b] | 83 (13.7)[b] |
| Neutropenia (grade ≥4) | 347 (57.7) | 384 (63.3) | 385 (63.3) |
| Febrile neutropenia | 21 (3.5) | 30 (4.9) | 26 (4.3) |
| Venous thromboembolic event | 35 (5.8) | 32 (5.3) | 41 (6.7) |
| Arterial thromboembolic event | 5 (0.8) | 4 (0.7) | 4 (0.7) |
| CNS bleeding | 0 | 0 | 2 (0.3) |
| Non-CNS bleeding (grade ≥3) | 5 (0.8) | 8 (1.3) | 13 (2.1) |
| RPLS | 0 | 1 (0.2) | 1 (0.2) |

RPLS = reversible posterior leukoencephalopathy syndrome
[a]Perforation/fistula/necrosis/leak
[b]$p<0.05$

FIG. 3

Select Adverse Events by Treatment Phase

| Select Adverse Events, n (Grade When Limited) | Arm I CP | | Arm II CP + BEV | | Arm III CP + BEV → BEV | |
|---|---|---|---|---|---|---|
| Patients, n Cycles, n | (n=601) | (n=483) | (n=607) | (n=457) | (n=608) | (n=464) |
| Treatment Phase[a] | Cytotoxic (Cycles 2-6) | Maintenance (Cycles ≥7) | Cytotoxic (Cycles 2-6) | Maintenance (Cycles ≥7) | Cytotoxic (Cycles 2-6) | Maintenance (Cycles ≥7) |
| GI events[b] (grade ≥2) | 6 | 1 | 16 | 1 | 15 | 1 |
| Hypertension (grade ≥3) | 3 | 7 | 24 | 12 | 25 | 38 |
| Proteinuria (grade ≥3) | 2 | 2 | 4 | 0 | 0 | 10 |
| Pain (grade ≥3) | 28 | 23 | 42 | 31 | 46 | 37 |
| Neutropenia (grade ≥4) | 345 | 2 | 382 | 2 | 385 | 0 |
| Febrile neutropenia | 21 | 0 | 30 | 0 | 26 | 0 |
| Venous thromboembolic event | 26 | 9 | 27 | 5 | 27 | 14 |
| Arterial thromboembolic event | 4 | 1 | 1 | 3 | 3 | 1 |
| CNS bleeding | 0 | 0 | 0 | 0 | 0 | 2 |
| Non-CNS bleeding (grade ≥3) | 3 | 2 | 8 | 0 | 10 | 3 |
| RPLS | 0 | 0 | 1 | 0 | 0 | 1 |

[a]Onset within 30 days of last treatment
[a]Perforation/fistula/necrosis/leak

*FIG. 4*

Ramifications of Using CA-125 as Determinant of Progression

| | Protocol-defined PFS Analysis | CA-125-censored PFS Analysis |
|---|---|---|
| Median PFS, months | | |
|   CP (Arm I) | 10.3 | 12.0 |
|   CP + BEV → BEV (Arm III) | 14.1 | 18.0 |
| Absolute difference in median PFS (months) | 3.8 | 6.0 |
| Hazard ratio | 0.717 | 0.645 |
| Censored for CA-125, % | | |
|   CP (Arm I) | 0 | 20 |
|   CP + BEV → BEV (Arm III) | 0 | 29 |

PFS Analysis for ICON7 Trial

|  | CP (N=764) | CPB7.5+ (N=764) |
|---|---|---|
| Patients with event | 392 ( 51.3 %) | 367 ( 48.0 %) |
| Patients without events | 372 ( 48.7 %) | 397 ( 52.0 %) |
| Time to event (months) |  |  |
| Median# | 16.0 | 18.3 |
| 95% CI for Median# | [14.3;17.3] | [17.8;19.1] |
| Range## | 0.0 to 32.9 | 0.0 to 32.9 |
| p-Value (Log-Rank Test) | 0.0010* | |
| Hazard Ratio | 0.79 | |
| 95% CI | [0.68;0.91] | |

Study Schema

AUC = area under the concentration-time curve;
d = day; IV = intravenous; PD = progressive disease.

SEQUENCE LISTING

<160> NUMBER OF SEQ ID NOS: 2

<210> SEQ ID NO 1
<211> LENGTH: 123
<212> TYPE: PRT
<213> ORGANISM: Artificial sequence
<220> FEATURE:
<223> OTHER INFORMATION: Sequence is Synthesized

<400> SEQUENCE: 1

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Asn Tyr Gly Met Asn Trp Val Arg Gln Ala Pro Gly Lys Gly Leu
                35                  40                  45

Glu Trp Val Gly Trp Ile Asn Thr Tyr Thr Gly Glu Pro Thr Tyr
                50                  55                  60

Ala Ala Asp Phe Lys Arg Arg Phe Thr Phe Ser Leu Asp Thr Ser
                65                  70                  75

Lys Ser Thr Ala Tyr Leu Gln Met Asn Ser Leu Arg Ala Glu Asp
                80                  85                  90

Thr Ala Val Tyr Tyr Cys Ala Lys Tyr Pro His Tyr Tyr Gly Ser
                95                 100                 105

Ser His Trp Tyr Phe Asp Val Trp Gly Gln Gly Thr Leu Val Thr
               110                 115                 120

Val Ser Ser
```

<210> SEQ ID NO 2
<211> LENGTH: 108
<212> TYPE: PRT
<213> ORGANISM: Artificial sequence
<220> FEATURE:
<223> OTHER INFORMATION: Sequence is Synthesized

<400> SEQUENCE: 2

```
Asp Ile Gln Met Thr Gln Ser Pro Ser Ser Leu Ser Ala Ser Val
 1               5                  10                  15

Gly Asp Arg Val Thr Ile Thr Cys Ser Ala Ser Gln Asp Ile Ser
                20                  25                  30

Asn Tyr Leu Asn Trp Tyr Gln Gln Lys Pro Gly Lys Ala Pro Lys
                35                  40                  45

Val Leu Ile Tyr Phe Thr Ser Ser Leu His Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Thr Val Pro Trp Thr Phe Gly Gln Gly Thr Lys Val Glu
                95                 100                 105

Ile Lys Arg
```

ANTI-ANGIOGENESIS THERAPY FOR THE TREATMENT OF OVARIAN CANCER

RELATED APPLICATIONS

This application claims priority to and the benefit of U.S. Provisional Application Ser. No. 61/439,819, filed Feb. 4, 2011, U.S. Provisional Application Ser. No. 61/360,059, filed Jun. 30, 2010, U.S. Provisional Application Ser. No. 61/351,231, filed Jun. 3, 2010, and U.S. Provisional Application Ser. No. 61/307,095, filed Feb. 23, 2010, the specifications of which are incorporated herein in their entirety.

FIELD OF THE INVENTION

This invention relates in general to treatment of human diseases and pathological conditions. More specifically, the invention relates to anti-angiogenesis therapy, either alone or in combination with other anti-cancer therapies, for the treatment of ovarian cancer.

BACKGROUND

Cancer remains to be one of the most deadly threats to human health. In the U.S., cancer affects nearly 1.3 million new patients each year, and is the second leading cause of death after heart disease, accounting for approximately 1 in 4 deaths. For women with ovarian and peritoneal cancer, after initial surgical diagnosis, staging and cytoreduction, the standard primary systemic chemotherapy for women with advanced epithelial ovarian, and peritoneal primary cancer consists of chemotherapy with a platinum and taxane combination, usually carboplatin and paclitaxel. See, e.g., McGuire W P, et al. *Cyclophosphamide and cisplatin compared with paclitaxel and cisplatin in patients with stage III and stage IV ovarian cancer. N Eng J Med* 334:1-6, 1996; Piccart M J, et al. *Randomized intergroup trial of cisplatin-paclitaxel versus cisplatin-cyclophamide in women with advanced epithelial ovarian cancer: three-year results. J Natl Cancer Inst* 92:699-708, 20003; Alberts D S, et al. *Improved therapeutic index of carboplatin plus cyclophosphamide versus cisplatin plus cyclophosphamide: final report by the Southwest Oncology Group of a phase III randomized trial in stages III and IV ovarian cancer. J Clin Oncol* 10:706-17, 1992; du Bois A, et al. *A randomized clinical trial of cisplatin/paclitaxel versus carboplatin/paclitaxel as first-line treatment of ovarian cancer.* J Natl Cancer Inst Sep. 3; 95.(17):1320.-9. 95:1320, 2003; Ozols R F, et al. *Phase III trial of carboplatin and paclitaxel compared with cisplatin and paclitaxel in patients with optimally resected stage III ovarian cancer: a Gynecologic Oncology Group study. J Clin Oncol* 21:3194-200, 2003; and, Swenerton K, et al. *Cisplatin-cyclophosphamide versus carboplatin-cyclophosphamide in advanced ovarian cancer: a randomized phase III study of the National Cancer Institute of Canada Clinical Trials Group. J Clin Oncol* 10:718-26, 1992. While advances have been made in patient management, this disease still carries a high fatality to case ratio for all gynecologic malignancies diagnosed in the United States. It is estimated that in 2004, 25,580 new cases will have been diagnosed and 16,090 women will have died of the disease. See, e.g., Jemal A, et al. *Cancer statistics, 2004. CA Cancer J Clin* 54:8-29, 2004. Improvements are needed in primary therapeutic strategies.

Angiogenesis is an important cellular event in which vascular endothelial cells proliferate, prune and reorganize to form new vessels from preexisting vascular network. There are compelling evidences that the development of a vascular supply is essential for normal and pathological proliferative processes (Folkman and Klagsbrun *Science* 235:442-447 (1987)). Delivery of oxygen and nutrients, as well as the removal of catabolic products, represent rate-limiting steps in the majority of growth processes occurring in multicellular organisms.

While induction of new blood vessels is considered to be the predominant mode of tumor angiogenesis, recent data have indicated that some tumors may grow by co-opting existing host blood vessels. The co-opted vasculature then regresses, leading to tumor regression that is eventually reversed by hypoxia-induced angiogenesis at the tumor margin. Holash et al. *Science* 284:1994-1998 (1999).

One of the key positive regulators of both normal and abnormal angiogenesis is vascular endothelial growth factor (VEGF)-A. VEGF-A is part of a gene family including VEGF-B, VEGF-C, VEGF-D, VEGF-E, VEGF-F, and PlGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. Additionally, neuropilin-1 has been identified as a receptor for heparin-binding VEGF-A isoforms, and may play a role in vascular development.

In addition to being an angiogenic factor in angiogenesis and vasculogenesis, VEGF, as a pleiotropic growth factor, exhibits multiple biological effects in other physiological processes, such as endothelial cell survival, vessel permeability and vasodilation, monocyte chemotaxis and calcium influx. Ferrara and Davis-Smyth (1997), supra. Moreover, studies have reported mitogenic effects of VEGF on a few non-endothelial cell types, such as retinal pigment epithelial cells, pancreatic duct cells and Schwann cells. Guerrin et al. *J. Cell Physiol.* 164:385-394 (1995); Oberg-Welsh et al. *Mol. Cell. Endocrinol.* 126:125-132 (1997); Sondell et al. *J. Neurosci.* 19:5731-5740 (1999). VEGF expression is upregulated in a majority of malignancies and the overexpression of VEGF often correlates with a more advanced stage or with a poorer prognosis in many solid tumors.

Since ovarian cancer is still one of the most deadly threats, additional cancer treatments for patients are needed. The invention addresses these and other needs, as will be apparent upon review of the following disclosure.

SUMMARY

Provided is the use of anti-VEGF antagonists for treating ovarian cancer. For example, uses of anti-VEGF antibodies for effectively treating women with newly diagnosed, previously untreated ovarian, fallopian tube or primary peritoneal cancer or platinum sensitive recurrent (or previously treated) ovary, primary, peritoneal, or fallopian tube carcinoma are provided. Data is provided from a randomized phase III clinical trial of bevacizumab (AVASTIN®) in combination with chemotherapy regimes in subjects (e.g., women) with newly diagnosed, previously untreated stage III (sub optimally and macroscopic optimally debulked) and IV epithelial ovarian, primary peritoneal or fallopian tube cancer (Example 1). Data is also provided from a randomized phase III clinical trial of bevacizumab (AVASTIN®) in combination with chemotherapy regimes in subjects (e.g., women) with newly diagnosed, high risk stage I and IIa (Grade 3 or clear cell carcinoma only) and stage IIb-IV epithelial ovarian, fallopian tube or primary peritoneal cancer, who have undergone initial surgery and who would not be considered for cytoreductive surgery prior to disease progression (Example 2). Data is also provided from a placebo-controlled, randomized, multicenter Phase III study evaluating the efficacy and safety of bevacizumab (15 mg/kg, Day 1, every 21 days), administered in combination with carboplatin (area under the curve [AUC] 4, Day 1, every 21 days) with gemcitabine (1000 mg/m$^2$, Day 1 and Day 8, every 21 days) in women with platinum sensitive recurrent epithelial ovarian, primary peritoneal, or fallopian tube carcinoma (Example 3). Such chemotherapy regimes include taxane therapy (e.g., paclitaxel or docetaxel), platinum based chemotherapy (e.g., carboplatin) or gemcitabine, and combinations thereof. The success of the trials show that providing anti-VEGF antibody (e.g., bevacizumab) when combined with chemotherapy and continued as maintenance therapy provides statistically significant and clinically meaningful benefits to ovarian cancer patients.

The results obtained in clinical studies of the use of bevacizumab in both concurrent and maintenance treatment in human subjects with previously untreated and recurrent ovarian cancer show that the efficacy, as evaluated by progression free survival (PFS) was positive especially when compared to PFS data for treatment with chemotherapeutic agents alone. Subjects in the clinical trials who received bevacizumab in concurrent treatment in combination with taxane therapy (e.g., paclitaxel or docetaxel), and platinum based chemotherapy (e.g., carboplatin) or platinum based chemotherapy (e.g., carboplatin) and gemcitabine and maintenance therapy with bevacizumab had an increase in progression free survival compared to subjects treated with taxane therapy (e.g., paclitaxel or docetaxel), and platinum based chemotherapy (e.g., carboplatin) alone or platinum based chemotherapy (e.g., carboplatin) and gemcitabine alone.

Accordingly, the invention provides a method of treating a patient diagnosed with previously untreated or recurrent ovarian cancer, comprising subjecting the patient to a treatment regimen combining at least one chemotherapy with the administration of an effective amount of an anti-VEGF antibody, and then administering the anti-VEGF antibody for maintenance therapy wherein with said treatment the progression free survival of the patient is increased. The treatment regimen combining the chemotherapy with the administration of the anti-VEGF and then the administration of anti-VEGF maintenance therapy effectively extends the progression free survival (PFS) of the patient.

In certain embodiments, the PFS is extended about 1 month, 1.2 months, 2 months, 2.9 months, 3 months, 3.8 months, 4 months, 6 months, 7 months, 8 months, 9 months, 1 year, about 2 years, about 3 years, etc, compared to a control. In one embodiment, the PFS is extended about 2.9 months to 3.8 months (e.g., with the treatment regimen combining the chemotherapy with the administration of the anti-VEGF and then the administration of anti-VEGF maintenance therapy) compared to a control. In one embodiment, the PFS is extended at least about 3.8 months (e.g., with the treatment regimen combining the chemotherapy with the administration of the anti-VEGF and then the administration of anti-VEGF maintenance therapy) compared to a control. In another embodiment, the PFS is extended about 2.3 months (e.g., with the treatment regimen combining the chemotherapy with the administration of the anti-VEGF and then the administration of anti-VEGF maintenance therapy) compared to a control. In one embodiment, the PFS is extended about 6 months (e.g., with the treatment regimen combining the chemotherapy with the administration of the anti-VEGF and then the administration of anti-VEGF maintenance therapy) compared to a control.

Any chemotherapeutic agent exhibiting anticancer activity can be used according to the present invention. In certain embodiments, the chemotherapeutic agent is selected from the group consisting of alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitor, interferons, platinum cordination complexes, taxanes anthracenedione substituted urea, methyl hydrazine derivatives, adrenocortical suppressant, adrenocorticosteroides, progestins, estrogens, antiestrogen, androgens, antiandrogen, gemcitabine and gonadotropin-releasing hormone analog. In certain embodiments, the chemotherapeutic agent is for example, taxane, paclitaxel, docetaxel, paclitaxel protein-bound particles (e.g., Abraxane®), gemcitabine, platinum analogs, carboplatin, or combinations thereof. Two or more chemotherapeutic agents can be used in a cocktail to be administered in combination with administration of the anti-VEGF antibody, e.g., taxane and platinum analogs or gemcitabine and platinum analogs. In one embodiment, it is carboplatin and paclitaxel. In one embodiment, it is carboplatin and docetaxel. In another embodiment, it is gemcitabine and carboplatin.

Clinical benefits of the treatments according to the invention can be measured by, for example, duration of progression free survival (PFS), time to treatment failure, objective response rate and duration of response.

Kits are also provided. In one embodiment, a kit is provided for treating previously untreated ovarian cancer in a human patient comprising a package comprising an anti-VEGF antibody composition and instructions for using the anti-VEGF antibody composition in combination with taxane therapy and carboplatin followed by anti-VEGF maintenance therapy, wherein the instructions recite that the progression free survival for patients receiving taxane therapy and carboplatin therapy and bevacizumab is 14.1 months with a hazard ratio of 0.717 (p-value<0.0001). In another embodiment, a kit is provided for treating previously untreated ovarian cancer in a human patient comprising a package comprising an anti-VEGF antibody composition and instructions for using the anti-VEGF antibody composition in combination with paclitaxel and carboplatin followed by anti-VEGF maintenance therapy, wherein the instructions recite that the progression free survival for patients receiving paclitaxel, carboplatin and anti-VEGF antibody is 18.3 months with a hazard ratio of 0.79. In certain embodiments, a kit comprises an anti-VEGF antibody that has a heavy chain variable region comprising the following amino acid sequence:

```
                                        (SEQ ID No. 1)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS
``` and a light chain variable region comprising the following amino acid sequence:

```
                                        (SEQ ID No. 2)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
```

In certain embodiments, the anti-VEGF antibody is bevacizumab in the kit. In certain embodiments, the kit is for a patient that has stage III or IV ovarian cancer.

Accordingly, the invention features a method of instructing a human subject with, e.g., ovarian, cancer by providing instructions to receive treatment with an anti-VEGF antibody so as to increase progression free survival of the subject, to decrease the subject's risk of cancer recurrence or to increase the subject's likelihood of survival. In some embodiments the method further comprises providing instructions to receive treatment with at least one chemotherapeutic agent. In some embodiments, the method further comprises providing instructions to receive treatment with at least two chemotherapeutic agents. In certain embodiments, the treatment with the anti-VEGF antibody is both concurrent and sequential to the treatment with the chemotherapeutic agent. In certain embodiments the subject is treated as instructed by the method of instructing.

The invention also provides a promotional method, comprising promoting the administration of an anti-VEGF antibody for treatment of, e.g., ovarian, cancer in a human subject. In some embodiments the method further comprises promoting the administration of at least one chemotherapeutic agent. In certain embodiments of the invention, the administration of the anti-VEGF antibody is both concurrent and sequential to administration of the chemotherapeutic agent(s). Promotion may be conducted by any means available. In some embodiments the promotion is by a package insert accompanying a commercial formulation of the anti-VEGF antibody. The promotion may also be by a package insert accompanying a commercial formulation of the chemotherapeutic agent(s). Promotion may be by written or oral communication to a physician or health care provider. In some embodiments the promotion is by a package insert where the package inset provides instructions to receive concurrent therapy with an anti-VEGF antibody and at least one chemotherapy agent(s) and maintenance therapy with an anti-VEGF antibody. In some embodiments the promotion is followed by the treatment of the subject with an anti-VEGF antibody with one or more chemotherapeutic agent(s) followed by maintenance therapy with an anti-VEGF antibody.

The invention provides a business method, comprising marketing an anti-VEGF antibody for treatment of, e.g., ovarian, cancer in a human subject in combination with at least one chemotherapy agent followed by anti-VEGF maintenance therapy so as to increase progression free survival, or decrease the subject's likelihood of cancer recurrence or increase the subject's likelihood of survival. In some embodiments the marketing is followed by treatment of the subject with the anti-VEGF antibody with the chemotherapeutic agent(s) followed by anti-VEGF maintenance therapy. In some embodiments the method further comprises marketing two or more chemotherapeutic agents for use in combination with the anti-VEGF antibody followed by anti-VEGF maintenance therapy. In some embodiments the marketing is followed by treatment of the subject with the anti-VEGF antibody with the chemotherapeutic agents followed by anti-VEGF maintenance therapy.

Also provided is a business method, comprising marketing a chemotherapeutic agent in combination with an anti-VEGF antibody followed by anti-VEGF maintenance therapy for treatment of, e.g., ovarian, cancer in a human subject so as to increase progression free survival, or decrease the subject's likelihood of cancer recurrence or increase the subject's likelihood of survival. In some embodiments, the marketing is followed by treatment of the subject with the combination of the chemotherapeutic agent and the anti-VEGF antibody followed by the anti-VEGF maintenance therapy. Also provided is a business method, comprising marketing two or more chemotherapeutic agents in combination with an anti-VEGF antibody followed by anti-VEGF maintenance therapy for treatment of, e.g., ovarian, cancer in a human subject so as to increase progression free survival, or decrease the subject's likelihood of cancer recurrence or increase the subject's likelihood of survival. In some embodiments, the marketing is followed by treatment of the subject with the combination of the chemotherapeutic agents and the anti-VEGF antibody followed by anti-VEGF maintenance therapy.

In each of the methods of the invention the anti-VEGF antibody may be substituted with a VEGF specific antagonist, e.g., a VEGF receptor molecule or chimeric VEGF receptor molecule as described below. In certain embodiments, the anti-VEGF antibody is bevacizumab. The anti-VEGF antibody, or antigen-binding fragment thereof, can be a monoclonal antibody, a chimeric antibody, a fully human antibody, or a humanized antibody. Exemplary antibodies useful in the methods of the invention include bevacizumab (AVASTIN®), a G6 antibody, a B20 antibody, and fragments thereof. In certain embodiments, the anti-VEGF antibody has a heavy chain variable region comprising the following amino acid sequence:

```
                                            (SEQ ID No. 1)
   EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS
``` and a light chain variable region comprising the following amino acid sequence:

```
                                            (SEQ ID No. 2)
   DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
```

The antibody, or antigen-binding fragment thereof, can also be an antibody that lacks an Fc portion, an F(ab')$_2$, an Fab, or an Fv structure.

In one embodiment, the treatment is a combination of a VEGF-specific antagonist, e.g., anti-VEGF antibody, and at least one chemotherapeutic agent followed by VEGF antagonist maintenance therapy. In one embodiment, the treatment is a combination of a VEGF-specific antagonist, e.g., anti-VEGF antibody, and two or more chemotherapeutic agents followed by VEGF antagonist maintenance therapy.

Each of the methods or uses of the invention may be practiced in relation to the treatment of cancers including, but not limited to, carcinoma, lymphoma, blastoma, sarcoma, and leukemia. More particular examples of such cancers include ovarian cancer, ovarian primary peritoneal cancer, ovarian fallopian tube cancer, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, liver cancer, bladder cancer, hepatoma, breast cancer, colon cancer, colorectal cancer, endometrial or uterine carcinoma, salivary gland carcinoma, kidney cancer, liver cancer, prostate cancer, renal cancer, vulval cancer, thyroid cancer, hepatic carcinoma, gastric cancer, melanoma, and various types of head and neck cancer. In some embodiments, the subject has previously untreated ovarian cancer. In some embodiment, the subject has newly diagnosed previously untreated ovarian cancer. In some embodiments, the subject has newly diagnosed, previously untreated, stage III (sub optimally and macroscopic optimally debulked) and IV epithelial ovarian primary peritoneal or fallopian tube cancer. In some embodiments, the subject has platinum sensitive recurrent epithelial ovarian, primary peritoneal, or fallopian tube carcinoma.

Each of the above aspects can further include monitoring the subject for recurrence of the cancer. Monitoring can be accomplished, for example, by evaluating progression free survival (PFS) or overall survival (OS) or objective response rate (ORR). In one embodiment, the PFS is evaluated after initiation of treatment.

Depending on the type and severity of the disease, preferred dosages for the anti-VEGF antibody, e.g., bevacizumab, are described herein and can range from about 1 µg/kg to about 50 mg/kg, most preferably from about 5 mg/kg to about 15 mg/kg, including but not limited to 5 mg/kg, 7.5 mg/kg, 10 mg/kg or 15 mg/kg. The frequency of administration will vary depending on the type and severity of the disease. For repeated administrations over several days or longer, depending on the condition, the treatment is sustained until the cancer is treated or the desired therapeutic effect is achieved, as measured by the methods described herein or known in the art. In one example, the anti-VEGF antibody of the invention is administered once every week, every two weeks, or every three weeks, at a dose range from about 5 mg/kg to about 15 mg/kg, including but not limited to 5 mg/kg, 7.5 mg/kg, 10 mg/kg or 15 mg/kg. However, other dosage regimens may be useful. The progress of the therapy of the invention is easily monitored by conventional techniques and assays. In certain embodiments of the invention, anti-VEGF therapy is provided as maintenance therapy. In further embodiments, anti-VEGF therapy is provided for at least 14 months (including concurrent anti-VEGF therapy with chemotherapy and anti-VEGF maintenance therapy). In other embodiments, anti-VEGF therapy is provided for at least 12 months (including concurrent anti-VEGF therapy with chemotherapy and anti-VEGF maintenance therapy).

In additional embodiments of each of the above aspects, the VEGF-specific antagonist, e.g., anti-VEGF antibody, is administered locally or systemically (e.g., orally or intravenously). In other embodiments, one aspect of the treatment is with the VEGF-specific antagonist in a monotherapy or a monotherapy for the duration of the VEGF-specific antagonist treatment period, e.g., in extended treatment phase or maintenance therapy, as assessed by the clinician or described herein. In certain embodiments, the anti-VEGF maintenance therapy is given for at least cycles 7 through 22. In other embodiments, the anti-VEGF maintenance therapy is given for at least cycles 7 through 18.

In other embodiments, treatment with the VEGF-specific antagonist is in combination with an additional anti-cancer therapy, including but not limited to, surgery, radiation therapy, chemotherapy, differentiating therapy, biotherapy, immune therapy, an angiogenesis inhibitor, a cytotoxic agent and an anti-proliferative compound. Treatment with the VEGF-specific antagonist can also include any combination of the above types of therapeutic regimens. In some embodiments, the chemotherapeutic agent and the VEGF-specific antagonist are administered concurrently followed by anti-VEGF maintenance therapy. In some embodiments, two or more chemotherapeutic agents and the VEGF-specific antagonist are administered concurrently followed by anti-VEGF maintenance therapy.

In the embodiments which include an additional anti-cancer therapy, the subject can be further treated with the additional anti-cancer therapy before, during (e.g., simultaneously), or after administration of the VEGF-specific antagonist. In one embodiment, the VEGF-specific antagonist, administered either alone or with an anti-cancer therapy, can be administered as maintenance therapy.

Other features and advantages of the invention will be apparent from the following Detailed Description, the drawings, and the claims.

BRIEF DESCRIPTION OF THE DRAWINGS

FIG. 1 depicts the study design for the ovarian cancer trial described in Example 1.

FIG. 2 depicts a diagram of the study design for the ovarian cancer trial using bevacizumab (BEV) or placebo with various chemotherapies.

FIG. 3 depicts select adverse events from the trial depicted in FIG. 2.

FIG. 4 depicts select adverse events by treatment phase from the trial depicted in FIG. 2.

DETAILED DESCRIPTION

I. Definitions

Figure 5:
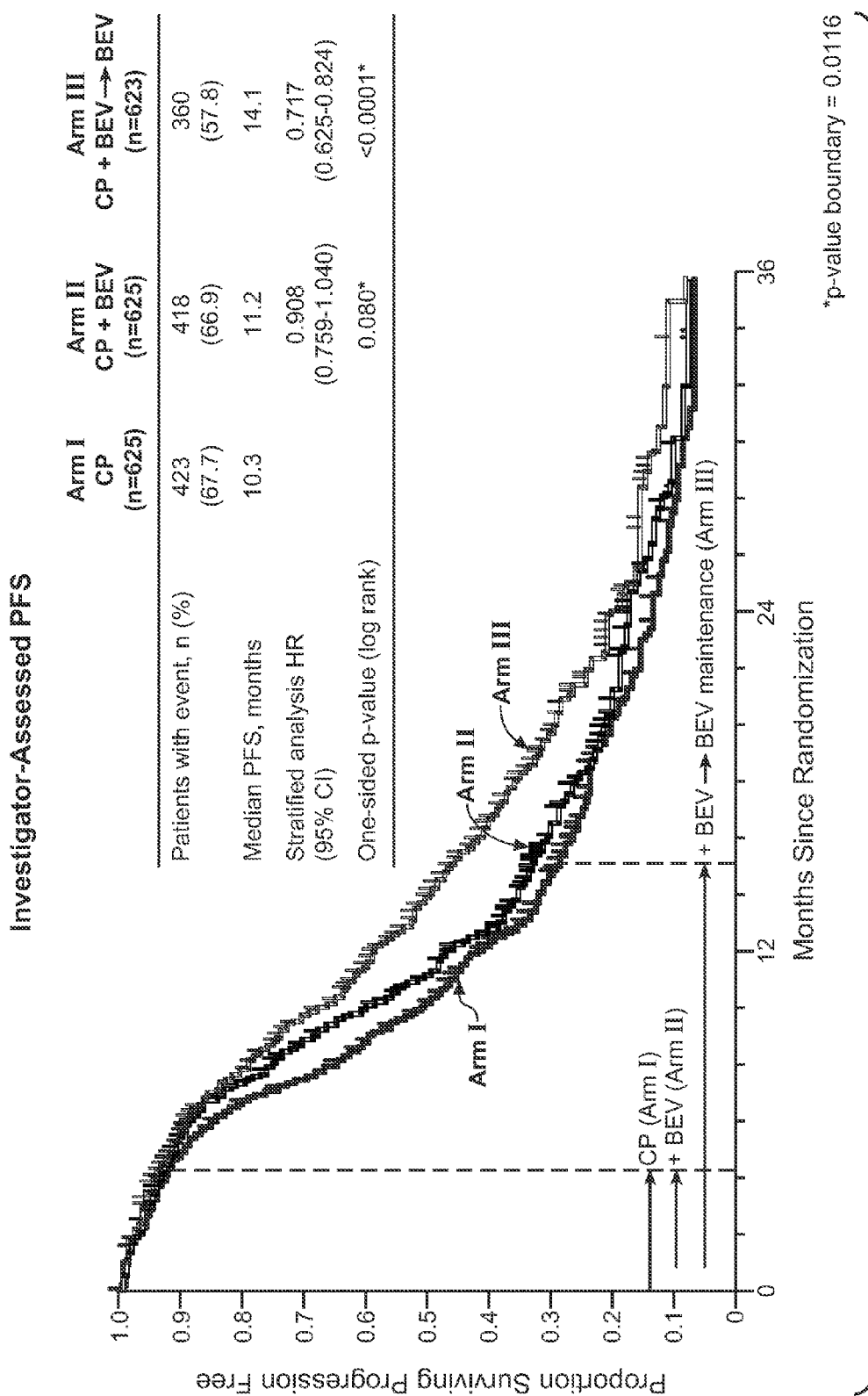
FIG. 5 depicts Investigator-assessed progression free survival (PFS) of Arm I, Arm II and Arm III of the trial depicted in FIG. 2.

The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. *Science,* 246:1306 (1989), and Houck et al. *Mol. Endocrin.,* 5:1806 (1991), together with the naturally occurring allelic and processed forms thereof. VEGF-A is part of a gene family including VEGF-B, VEGF-C, VEGF-D, VEGF-E, VEGF-F, and PlGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. Additionally, neuropilin-1 has been identified as a receptor for heparin-binding VEGF-A isoforms, and may play a role in vascular development. The term "VEGF" or "VEGF-A" also refers to VEGFs from non-human species such as mouse, rat, or primate. Sometimes the VEGF from a specific species is indicated by terms such as hVEGF for human VEGF or mVEGF for murine VEGF. The term "VEGF" is also used to refer to truncated forms or fragments of the polypeptide comprising amino acids 8 to 109 or 1 to 109 of the 165-amino acid human vascular endothelial cell growth factor. Reference to any such forms of VEGF may be identified in the application, e.g., by "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. The antibody selected will normally have a binding affinity for VEGF, for example, the antibody may bind hVEGF with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. In certain embodiments, the anti-VEGF antibody of the invention can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF or bFGF.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases.

A "native sequence" polypeptide comprises a polypeptide having the same amino acid sequence as a polypeptide derived from nature. Thus, a native sequence polypeptide can have the amino acid sequence of naturally-occurring polypeptide from any mammal. Such native sequence polypeptide can be isolated from nature or can be produced by recombinant or synthetic means. The term "native sequence" polypeptide specifically encompasses naturally-occurring truncated or secreted forms of the polypeptide (e.g., an extracellular domain sequence), naturally-occurring variant forms (e.g., alternatively spliced forms) and naturally-occurring allelic variants of the polypeptide.

A polypeptide "variant" means a biologically active polypeptide having at least about 80% amino acid sequence identity with the native sequence polypeptide. Such variants include, for instance, polypeptides wherein one or more amino acid residues are added, or deleted, at the N- or C-terminus of the polypeptide. Ordinarily, a variant will have at least about 80% amino acid sequence identity, more preferably at least about 90% amino acid sequence identity, and even more preferably at least about 95% amino acid sequence identity with the native sequence polypeptide.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments (see below) so long as they exhibit the desired biological activity.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

The "Kd" or "Kd value" according to this invention is in one embodiment measured by a radiolabeled VEGF binding assay (RIA) performed with the Fab version of the antibody and a VEGF molecule as described by the following assay that measures solution binding affinity of Fabs for VEGF by equilibrating Fab with a minimal concentration of ($^{125}$I)-labeled VEGF(109) in the presence of a titration series of unlabeled VEGF, then capturing bound VEGF with an anti-Fab antibody-coated plate (Chen, et al., (1999) *J. Mol Biol* 293:865-881). In one example, to establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I] VEGF(109) are mixed with serial dilutions of a Fab of interest, e.g., Fab-12 (Presta et al., (1997) *Cancer Res.* 57:4593-4599). The Fab of interest is then incubated overnight; however, the incubation may continue for 65 hours to insure that equilibrium is reached. Thereafter, the mixtures are transferred to the capture plate for incubation at room temperature for one hour. The solution is then removed and the plate washed eight times with 0.1% Tween-20 in PBS. When the plates had dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized hVEGF (8-109) CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Human VEGF is diluted with 10 mM sodium acetate, pH 4.8, into 5 ug/ml (~0.2 uM) before injection at a flow rate of 5 ul/minute to achieve approximately 10 response units (RU) of coupled protein. Following the injection of human VEGF, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) *J. Mol Biol* 293:865-881. If the on-rate exceeds $10^6$ $M^{-1}$ $S^{-1}$ by the surface plasmon resonance assay above, then the on-rate is can be determined by using a fluorescent quenching technique that measures the increase or decrease in fluorescence emission intensity (excitation=295 nm; emission=340 nm, 16 nm band-pass) at 25° C. of a 20 nM anti-VEGF antibody (Fab form) in PBS, pH 7.2, in the presence of increasing concentrations of human VEGF short form (8-109) or mouse VEGF as measured in a spectrometer, such as a stop-flow equipped spectrophometer (Aviv Instruments) or a 8000-series SLM-Aminco spectrophotometer (ThermoSpectronic) with a stirred cuvette.

A "blocking" antibody or an antibody "antagonist" is one which inhibits or reduces biological activity of the antigen it binds. For example, a VEGF-specific antagonist antibody binds VEGF and inhibits the ability of VEGF to induce vascular endothelial cell proliferation or to induce vascular permeability. In certain embodiments, the blocking antibodies or antagonist antibodies completely or substantially inhibit the biological activity of the antigen.

Unless indicated otherwise, the expression "multivalent antibody" is used throughout this specification to denote an antibody comprising three or more antigen binding sites. For example, the multivalent antibody is engineered to have the three or more antigen binding sites and is generally not a native sequence IgM or IgA antibody.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., *Nature* 341, 544-546 (1989)) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., *Science* 242:423-426 (1988); and Huston et al., *PNAS (USA)* 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., *Proc. Natl. Acad. Sci. USA*, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. *Protein Eng.* 8(10):1057-1062 (1995); and U.S. Pat. No. 5,641,870).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention may be made by the hybridoma method first described by Kohler et al., *Nature* 256:495 (1975), or may be made by recombinant DNA methods (see, e.g., U.S. Pat. No. 4,816, 567). The "monoclonal antibodies" may also be isolated from phage antibody libraries using the techniques described in Clackson et al., *Nature* 352:624-628 (1991) or Marks et al., *J. Mol. Biol.* 222:581-597 (1991), for example.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

The "Fab" fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The expression "linear antibodies" refers to the antibodies described in Zapata et al., *Protein Eng.*, 8(10):1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. *Nature Biotechnology* 14:309-314 (1996): Sheets et al. *Proc. Natl. Acad. Sci.* 95:6157-6162 (1998)); Hoogenboom and Winter, *J. Mol. Biol.*, 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al., *J. Mol. Biol.* 226:889-896 (1992).

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis as described in Example 2 of U.S. Patent Application Publication No. 20050186208. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but typically is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (e.g., Ghetie et al., *Ann. Rev. Immunol.* 18:739-766 (2000), Table 1). Antibodies with substitutions in an Fc region thereof and increased serum half-lives are also described in WO00/42072, WO 02/060919; Shields et al., *J. Biol. Chem.* 276: 6591-6604 (2001); Hinton, *J. Biol. Chem.* 279:6213-6216 (2004)). In another embodiment, the serum half-life can also be increased, for example, by attaching other polypeptide sequences. For example, antibodies or other polypeptides useful in the methods of the invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746. In one embodiment, the serum albumin peptide to be attached comprises an amino acid sequence of DICLPRWGCLW. In another embodiment, the half-life of a Fab is increased by these methods. See also, Dennis et al. *J. Biol. Chem.* 277: 35035-35043 (2002) for serum albumin binding peptide sequences.

A "chimeric VEGF receptor protein" is a VEGF receptor molecule having amino acid sequences derived from at least two different proteins, at least one of which is as VEGF receptor protein. In certain embodiments, the chimeric VEGF receptor protein is capable of binding to and inhibiting the biological activity of VEGF.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Anti-angiogensis agents also include native angiogenesis inhibitors, e.g., angiostatin, endostatin, etc. See, e.g., Klagsbrun and D'Amore, *Annu Rev. Physiol.,* 53:217-39 (1991); Streit and Detmar, *Oncogene,* 22:3172-3179 (2003) (e.g., Table 3 listing anti-angiogenic therapy in malignant melanoma); Ferrara & Alitalo, *Nature Medicine* 5:1359-1364 (1999); Tonini et al., *Oncogene,* 22:6549-6556 (2003) (e.g., Table 2 listing known antiangiogenic factors); and Sato. *Int. J. Clin. Oncol.,* 8:200-206 (2003) (e.g., Table 1 lists anti-angiogenic agents used in clinical trials).

Figure 8:
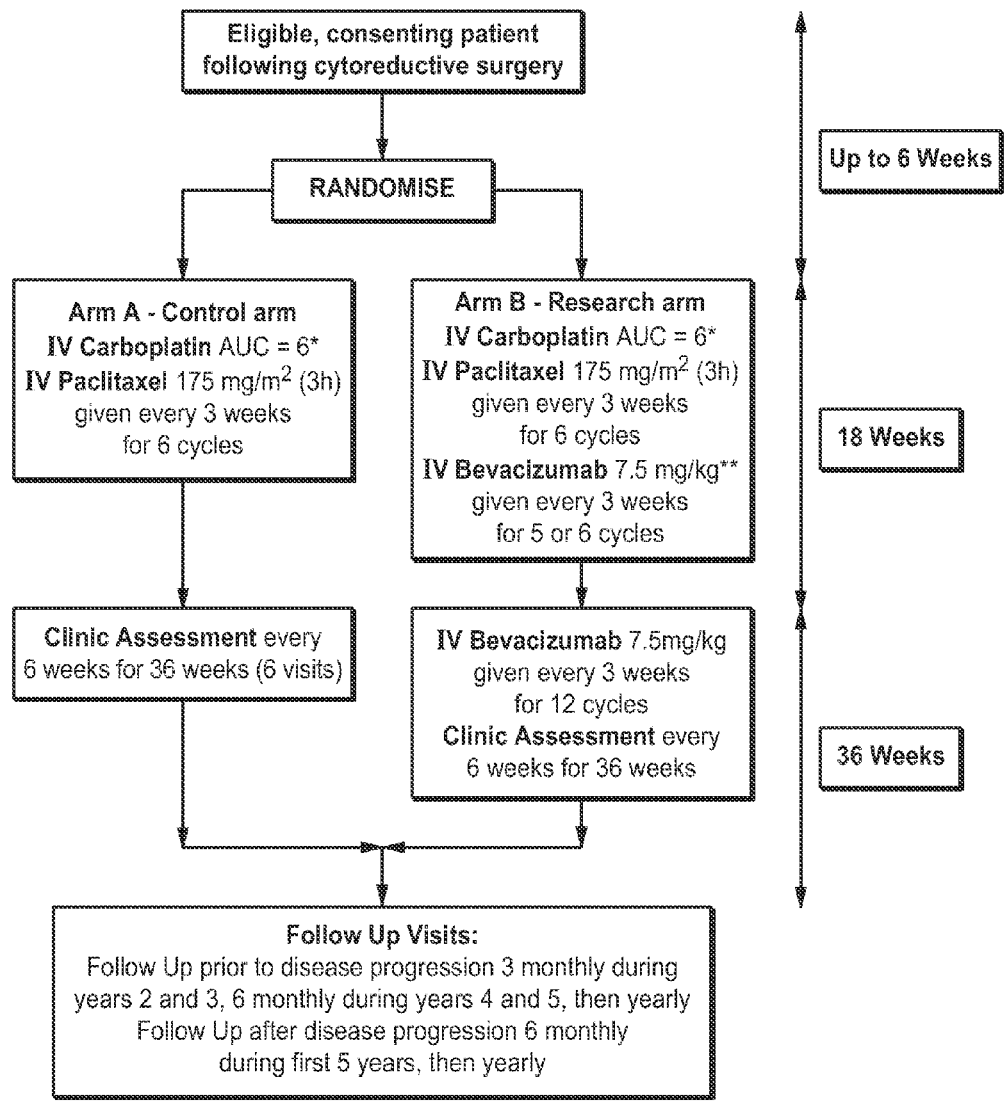
FIG. 8 depicts the study design for the ovarian cancer trial described in Example 2.
Figures 9, 11:
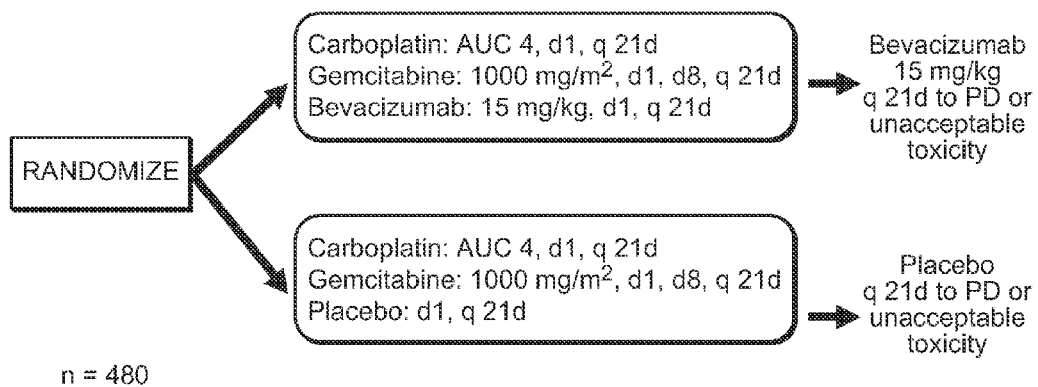
FIG. 9 depicts a summary of the progression free survival (PFS) analysis of the trial depicted in FIG. 8. "CP" corresponds to Arm A in FIG. 8. "CPB7.5+" corresponds to Arm B in FIG. 8.
FIG. 11 depicts the study design for the ovarian cancer trial described in Example 3.

A "maintenance" dose herein refers to one or more doses of a therapeutic agent administered to the patient over or after a treatment period. Usually, the maintenance doses are administered at spaced treatment intervals, such as approximately every week, approximately every 2 weeks, approximately every 3 weeks, or approximately every 4 weeks. In one embodiment, the maintenance doses are as depicted in FIG. 1 (extended therapy), FIG. 2 or FIG. 8 or FIG. 11 herein.

"Survival" refers to the patient remaining alive, and includes progression free survival (PFS) and overall survival (OS). Survival can be estimated by the Kaplan-Meier method, and any differences in survival are computed using the stratified log-rank test.

"Progression free survival (PFS)" refers to the time from treatment (or randomization) to first disease progression or death. In one aspect of the invention, PFS can be assessed by Response Evaluation Criteria in Solid Tumors (RECIST). In one aspect of the invention, PFS can be assessed by CA-125 levels as a determinant of progression.

"Overall survival" refers to the patient remaining alive for a defined period of time, such as about 1 year, about 1.5 years, about 2 years, about 3 years, about 4 years, about 5 years, about 10 years, etc., from initiation of treatment or from initial diagnosis. In the studies underlying the invention the event used for survival analysis was death from any cause.

By "extending survival" or "increasing the likelihood of survival" is meant increasing PFS and/or OS in a treated patient relative to an untreated patient (i.e. relative to a patient not treated with a VEGF-specific antagonist, e.g., a VEGF antibody), or relative to a control treatment protocol, such as treatment only with the chemotherapeutic agent, such as those use in the standard of care for ovarian cancer. For example extended PFS is the time that the patient remains alive, without return of the cancer, e.g., for a defined period of time such as about 1 month, 2 months, 2.3 months, 2.9 months, 3 months, 3.8 months, 4 months, 6 months, 7 months, 8 months, 9 months, 1 year, about 2 years, about 3 years, etc., from initiation of treatment or from initial diagnosis, compared to a control (e.g., patient not treated with the same VEGF specific antagonist). In one embodiment, the PFS is extended about 2.9 months to 3.8 months compared to a control. In one embodiment, the PFS is extended at least about 3.8 months compared to a control. In another embodiment, the PFS is extended by about 2.3 months. In one embodiment, the PFS is extended about 6 months compared to a control. In certain embodiment, survival is monitored for at least about one month, two months, four months, six months, nine months, or at least about 1 year, or at least about 2 years, or at least about 3 years, or at least about 4 years, or at least about 5 years, or at least about 10 years, etc., following the initiation of treatment or following the initial diagnosis.

Hazard ratio (HR) is a statistical definition for rates of events. For the purpose of the invention, hazard ratio is defined as representing the probability of an event in the experimental arm divided by the probability of an event in the control arm at any specific point in time. "Hazard ratio" in progression free survival analysis is a summary of the difference between two progression free survival curves, representing the reduction in the risk of death on treatment compared to control, over a period of follow-up.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "monotherapy" is meant a therapeutic regimen that includes only a single therapeutic agent for the treatment of the cancer or tumor during the course of the treatment period. Monotherapy using a VEGF-specific antagonist means that the VEGF-specific antagonist is administered in the absence of an additional anti-cancer therapy during treatment period.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy. In certain embodiments of the invention, maintenance therapy is provided for at least 16 cycles after completion of the chemotherapy concurrently with 5 cycles of anti-VEGF therapy. In other embodiments of the invention, maintenance therapy is provided for at least 12 cycles after completion of the chemotherapy concurrently with 6 cycles of anti-VEGF therapy. In one embodiment, maintenance therapy is as depicted in FIG. 1, FIG. 2, FIG. 8 or FIG. 11.

The terms "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, carcinoma, lymphoma, blastoma, sarcoma, and leukemia. More particular examples of such cancers include ovarian cancer, ovarian primary peritoneal cancer, ovarian fallopian tube cancer, platinum sensitive recurrent epithelial ovarian, primary peritoneal, or fallopian tube carcinoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

By "subject" is meant a mammal, including, but not limited to, a human or non-human mammal, such as a bovine, equine, canine, ovine, or feline. Preferably, the subject is a human. Patients are also subjects herein. Typically, the subject is female.

For the methods of the present invention, the term "instructing" a subject means providing directions for applicable therapy, medication, treatment, treatment regimens, and the like, by any means, but preferably in writing, such as in the form of package inserts or other written promotional material.

For the methods of the present invention, the term "promoting" means offering, advertising, selling, or describing a particular drug, combination of drugs, or treatment modality, by any means, including writing, such as in the form of package inserts. Promoting herein refers to promotion of a therapeutic agent, such as a VEGF antagonist, e.g., anti-VEGF antibody or chemotherapeutic agent, for an indication, such as ovarian cancer treatment, where such promoting is authorized by the Food and Drug Administration (FDA) as having been demonstrated to be associated with statistically significant therapeutic efficacy and acceptable safety in a population of subjects The term "marketing" is used herein to describe the promotion, selling or distribution of a product (e.g., drug). Marketing specifically includes packaging, advertising, and any business activity with the purpose of commercializing a product.

A "population" of subjects refers to a group of subjects with cancer, such as in a clinical trial, or as seen by oncologists following FDA approval for a particular indication, such as ovarian cancer therapy.

The term "anti-cancer therapy" refers to a therapy useful in treating cancer. Examples of anti-cancer therapeutic agents include, but are limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva®), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e. g., calicheamicin, especially calicheamicin gamma1I and calicheamicin omegaII (see, e.g., Agnew, *Chem Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY 117018, onapristone, and FARESTON• toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A. Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases or micrometastases, the size of the primary tumor, the presence or the size of the dormant tumor, or the size or number of the blood vessels in angiogenic disorders.

The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less.

The term "intravenous bolus" or "intravenous push" refers to drug administration into a vein of an animal or human such that the body receives the drug in approximately 15 minutes or less, preferably 5 minutes or less.

The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue, where the pocket is created, for example, by pinching or drawing the skin up and away from underlying tissue.

A "disorder" is any condition that would benefit from treatment with the antibody. This includes chronic and acute disorders or diseases including those pathological conditions which predispose the mammal to the disorder in question. Non-limiting examples of disorders to be treated herein include cancer; benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, duration of progression free survival (PFS), extension of progression free survival (PFS), the response rates (RR), duration of response, and/or quality of life.

"Treatment" refers to therapeutic treatment for those in need of treatment include those already with the disorder.

"Prophylactic or preventative treatment" refers to those in which the disorder is to be prevented.

The word "label" when used herein refers to a detectable compound or composition which is conjugated directly or indirectly to the polypeptide. The label may be itself be detectable (e.g., radioisotope labels or fluorescent labels) or, in the case of an enzymatic label, may catalyze chemical alteration of a substrate compound or composition which is detectable.

II. Anti-VEGF Antibodies and Antagonists

Uses of anti-VEGF antagonists for treating ovarian cancer are provided herein. Angiogenesis is one of the cardinal processes leading to invasion and metastasis of solid tumors. The angiogenic-signaling pathway may be triggered by the release of angiogenic promoters such as vascular endothelial growth factor (VEGF) from tumor cells into the local microenvironment. There is accumulating evidence that angiogenesis plays a role in ovarian cancer disease prognosis and possibly progression and prognosis. See, e.g., Yoneda J, et al., *Expression of angiogenesis-related genes and progression of human ovarian carcinomas in nude mice. J Natl Cancer Inst* 90:447-54, 1998; Nakanishi Y, et al. *The expression of vascular endothelial growth factor and transforming growth factor-beta associates with angiogenesis in epithelial ovarian cancer. Int J Gynecol Pathol* 16:256-62, 1997; Gasparini G, et al. *Prognostic and predictive value of tumour angiogenesis in ovarian carcinomas. Int J Cancer* 69:205-11, 1996; Hollingsworth H C, et al., *Tumor angiogenesis in advanced stage ovarian carcinoma. Am J Pathol* 147:33-41, 1995; Paley P J, et al. *Vascular endothelial growth factor expression in early stage ovarian carcinoma. Cancer* 80:98-106, 1997; Alvarez A A, et al., *The prognostic significance of angiogenesis in epithelial ovarian carcinoma. Clin Cancer Res* 5:587-91, 1999; Gasparini G. *The rationale and future potential of angiogenesis inhibitors in neoplasia. Drugs* 58:17-38, 1999; van Hinsbergh V W, et al., *Angiogenesis and anti-angiogenesis: perspectives for the treatment of solid tumors. Ann Oncol* 10 Suppl 4:60-3, 1999; Malonne H, et al., *Mechanisms of tumor angiogenesis and therapeutic implications: angiogenesis inhibitors. Clin Exp Metastasis* 17:1-14, 1999; Folkman J. *Tumor angiogenesis: therapeutic implications. N Eng J Med* 285:1182-6, 1971; Kim K J, et al. *Inhibition of vascular endothelial growth factor-induced angiogenesis suppresses tumour growth in vivo. Nature* 362:841-4, 1993; and, Luo J C, et al., *Differential inhibition of fluid accumulation and tumor growth in two mouse ascites tumors by an anti vascular endothelial growth factor/permeability factor neutralizing antibody. Cancer Res* 58:2594-600, 1998.

(i) VEGF Antigen

The VEGF antigen to be used for production of antibodies may be, e.g., the $VEGF_{165}$ molecule as well as other isoforms of VEGF or a fragment thereof containing the desired epitope. Other forms of VEGF useful for generating anti-VEGF antibodies of the invention will be apparent to those skilled in the art.

Human VEGF was obtained by first screening a cDNA library prepared from human cells, using bovine VEGF cDNA as a hybridization probe. Leung et al. (1989) *Science*, 246:1306. One cDNA identified thereby encodes a 165-amino acid protein having greater than 95% homology to bovine VEGF; this 165-amino acid protein is typically referred to as human VEGF (hVEGF) or VEGF$_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung et al. (1989) *Science*, supra.

Although a vascular endothelial cell growth factor could be isolated and purified from natural sources for subsequent therapeutic use, the relatively low concentrations of the protein in follicular cells and the high cost, both in terms of effort and expense, of recovering VEGF proved commercially unavailing. Accordingly, further efforts were undertaken to clone and express VEGF via recombinant DNA techniques. (See, e.g., Ferrara, *Laboratory Investigation* 72:615-618 (1995), and the references cited therein).

VEGF is expressed in a variety of tissues as multiple homodimeric forms (121, 145, 165, 189, and 206 amino acids per monomer) resulting from alternative RNA splicing. VEGF$_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. Amino acid sequencing of the carboxy terminal peptide identified after plasmin cleavage is Arg$_{110}$-Ala$_{111}$. Amino terminal "core" protein, VEGF (1-110) isolated as a homodimer, binds neutralizing monoclonal antibodies (such as the antibodies referred to as 4.6.1 and 3.2E3.1.1) and soluble forms of VEGF receptors with similar affinity compared to the intact VEGF$_{165}$ homodimer.

Several molecules structurally related to VEGF have also been identified including placenta growth factor (PlGF), VEGF-B, VEGF-C, VEGF-D and VEGF-E. Ferrara and Davis-Smyth (1987) *Endocr. Rev.*, supra; Ogawa et al. *J. Biological Chem.* 273:31273-31281(1998); Meyer et al. *EMBO J.*, 18:363-374(1999). A receptor tyrosine kinase, Flt-4 (VEGFR-3), has been identified as the receptor for VEGF-C and VEGF-D. Joukov et al. *EMBO. J.* 15:1751 (1996); Lee et al. *Proc. Natl. Acad. Sci. USA* 93:1988-1992 (1996); Achen et al. (1998) *Proc. Natl. Acad. Sci. USA* 95:548-553. VEGF-C has been shown to be involved in the regulation of lymphatic angiogenesis. Jeltsch et al. *Science* 276:1423-1425(1997).

(ii) Anti-VEGF Antibodies

Anti-VEGF antibodies that are useful in the methods of the invention to treat ovarian cancer include any antibody, or antigen binding fragment thereof, that bind with sufficient affinity and specificity to VEGF and can reduce or inhibit the biological activity of VEGF. An anti-VEGF antibody will usually not bind to other VEGF homologues such as VEGF-B or VEGF-C, nor other growth factors such as PlGF, PDGF, or bFGF.

In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) *Cancer Res.* 57:4593-4599. In one embodiment, the anti-VEGF antibody is "Bevacizumab (BV)", also known as "rhuMAb VEGF" or "AVASTIN®". AVASTIN® is commercially available in certain countries. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1.

Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference. For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004). Other antibodies include those that bind to a functional epitope on human VEGF comprising of residues F17, M18, D19, Y21, Y25, Q89, I91, K101, E103, and C104 or, alternatively, comprising residues F17, Y21, Q22, Y25, D63, I83 and Q89.

In one embodiment of the invention, the anti-VEGF antibody has a heavy chain variable region comprising the following amino acid sequence:

```
                                               (SEQ ID No. 1)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS
``` and a light chain variable region comprising the following amino acid sequence:

```
                                               (SEQ ID No. 2)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
```

A "G6 series antibody" according to this invention, is an anti-VEGF antibody that is derived from a sequence of a G6 antibody or G6-derived antibody according to any one of FIGS. 7, 24-26, and 34-35 of PCT Publication No. WO2005/012359, the entire disclosure of which is expressly incorporated herein by reference. See also PCT Publication No. WO2005/044853, the entire disclosure of which is expressly incorporated herein by reference. In one embodiment, the G6 series antibody binds to a functional epitope on human VEGF comprising residues F17, Y21, Q22, Y25, D63, I83 and Q89.

A "B20 series antibody" according to this invention is an anti-VEGF antibody that is derived from a sequence of the B20 antibody or a B20-derived antibody according to any one of FIGS. 27-29 of PCT Publication No. WO2005/012359, the entire disclosure of which is expressly incorporated herein by reference. See also PCT Publication No. WO2005/044853, and U.S. Patent Application 60/991,302, the content of these patent applications are expressly incorporated herein by reference. In one embodiment, the B20 series antibody binds to a functional epitope on human VEGF comprising residues F17, M18, D19, Y21, Y25, Q89, I91, K101, E103, and C104.

A "functional epitope" according to this invention refers to amino acid residues of an antigen that contribute energetically to the binding of an antibody. Mutation of any one of the energetically contributing residues of the antigen (for example, mutation of wild-type VEGF by alanine or homolog mutation) will disrupt the binding of the antibody such that the relative affinity ratio (IC50mutant VEGF/IC50wild-type VEGF) of the antibody will be greater than 5 (see Example 2 of WO2005/012359). In one embodiment, the relative affinity ratio is determined by a solution binding phage displaying ELISA. Briefly, 96-well Maxisorp immunoplates (NUNC) are coated overnight at 4° C. with an Fab form of the antibody to be tested at a concentration of 2 ug/ml in PBS, and blocked with PBS, 0.5% BSA, and 0.05% Tween20 (PBT) for 2 h at room temperature. Serial dilutions of phage displaying hVEGF alanine point mutants (residues 8-109 form) or wild type hVEGF (8-109) in PBT are first incubated on the Fab-coated plates for 15 min at room temperature, and the plates are washed with PBS, 0.05% Tween20 (PBST). The bound phage is detected with an anti-M13 monoclonal antibody horseradish peroxidase (Amersham Pharmacia) conjugate diluted 1:5000 in PBT, developed with 3,3',5,5'-tetramethyl-benzidine (TMB, Kirkegaard & Perry Labs, Gaithersburg, Md.) substrate for approximately 5 min, quenched with 1.0 M $H_3PO_4$, and read spectrophotometrically at 450 nm. The ratio of IC50 values (IC50,ala/IC50,wt) represents the fold of reduction in binding affinity (the relative binding affinity).

(iii) VEGF Receptor Molecules

Two VEGF receptors have been identified, Flt-1 (also called VEGFR-1) and KDR (also called VEGFR-2). Shibuya et al. (1990) *Oncogene* 8:519-527; de Vries et al. (1992) *Science* 255:989-991; Terman et al. (1992) *Biochem. Biophys. Res. Commun.* 187:1579-1586. The specificity of each receptor for each VEGF family member varies but VEGF-A binds to both Flt-1 and KDR. Neuropilin-1 has been shown to be a selective VEGF receptor, able to bind the heparin-binding VEGF isoforms (Soker et al. (1998) *Cell* 92:735-45). Both Flt-I and KDR belong to the family of receptor tyrosine kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich (1988) *Ann. Rev. Biochem.* 57:433-478; Ullrich and Schlessinger (1990) *Cell* 61:243-254). The intrinsic function of RTKs is activated upon ligand binding, which results in phosphorylation of the receptor and multiple cellular substrates, and subsequently in a variety of cellular responses (Ullrich & Schlessinger (1990) *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see, Schlessinger and Ullrich (1992) *Neuron* 9:1-20. Structurally, both Flt-1 and KDR have seven immunoglobulin-like domains in the extracellular domain, a single transmembrane region, and a consensus tyrosine kinase sequence which is interrupted by a kinase-insert domain. Matthews et al. (1991) *Proc. Natl. Acad. Sci. USA* 88:9026-9030; Terman et al. (1991) *Oncogene* 6:1677-1683.

VEGF receptor molecules, or fragments thereof, that specifically bind to VEGF can be used in the methods of the invention to bind to and sequester the VEGF protein, thereby preventing it from signaling. In certain embodiments, the VEGF receptor molecule, or VEGF binding fragment thereof, is a soluble form, such as sFlt-1. A soluble form of the receptor exerts an inhibitory effect on the biological activity of the VEGF protein by binding to VEGF, thereby preventing it from binding to its natural receptors present on the surface of target cells. Also included are VEGF receptor fusion proteins, examples of which are described below.

A chimeric VEGF receptor protein is a receptor molecule having amino acid sequences derived from at least two different proteins, at least one of which is a VEGF receptor protein (e.g., the flt-1 or KDR receptor), that is capable of binding to and inhibiting the biological activity of VEGF. In certain embodiments, the chimeric VEGF receptor proteins of the invention consist of amino acid sequences derived from only two different VEGF receptor molecules; however, amino acid sequences comprising one, two, three, four, five, six, or all seven Ig-like domains from the extracellular ligand-binding region of the flt-1 and/or KDR receptor can be linked to amino acid sequences from other unrelated proteins, for example, immunoglobulin sequences. Other amino acid sequences to which Ig-like domains are combined will be readily apparent to those of ordinary skill in the art. Examples of chimeric VEGF receptor proteins include, e.g., soluble Flt-1/Fc, KDR/Fc, or FLt-1/KDR/Fc (also known as VEGF Trap). (See for example PCT Application Publication No. WO97/44453)

A soluble VEGF receptor protein or chimeric VEGF receptor proteins of the invention includes VEGF receptor proteins which are not fixed to the surface of cells via a transmembrane domain. As such, soluble forms of the VEGF receptor, including chimeric receptor proteins, while capable of binding to and inactivating VEGF, do not comprise a transmembrane domain and thus generally do not become associated with the cell membrane of cells in which the molecule is expressed.

III. Therapeutic Uses of Anti-VEGF Antibodies

The invention encompasses antiangiogenic therapy, a novel cancer treatment strategy aimed at inhibiting the development of tumor blood vessels required for providing nutrients to support tumor growth. Because angiogenesis is involved in both primary tumor growth and metastasis, the antiangiogenic treatment provided by the invention is capable of inhibiting the neoplastic growth of tumor at the primary site as well as preventing metastasis of tumors at the secondary sites, therefore allowing attack of the tumors by other therapeutics. In addition, ovarian cancer is associated with a high level of circulating vascular endothelial growth factor (VEGF), a protein associated with tumor growth and spread. Studies of women with ovarian cancer have shown a correlation between a high level of VEGF and a poorer prognosis (Alvarez A et al. 1999 *Clin Cancer Res.;* 5:587-591; Yamamoto S et al. 1997 *Br J Cancer* 76:1221-1227).

Specifically, in one embodiment, the invention provides a method of treating a patient diagnosed with (optionally newly diagnosed), previously untreated ovarian cancer, comprising subjecting the patient to a treatment regimen combining at least chemotherapy concurrent with the administration of an effective amount of an anti-VEGF antibody followed by anti-VEGF maintenance therapy. In certain embodiments of the invention, the patient has stage III (sub optimally and macroscopic optimally debulked) or stage IV epithelial ovarian primary peritoneal or fallopian tube cancer. In other embodiments, the patient has stage I and IIa (Grade 3 or clear cell carcinoma only) or stage IIb-IV epithelial ovarian, fallopian tube or primary peritoneal cancer. In another embodiment, the invention provides a method of treating a patient diagnosed with recurrent or previously treated ovarian cancer, comprising subjecting the patient to a treatment regimen combining at least chemotherapy concurrent with the administration of an effective amount of an anti-VEGF antibody followed by anti-VEGF maintenance therapy.

Combination Therapies

The invention features the use of a combination of at least one VEGF-specific antagonist with one or more additional anti-cancer therapies followed by anti-VEGF maintenance therapy. Examples of anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents can be used in combination with the VEGF-specific antagonist.

In certain aspects, the invention provides a method of treating ovarian cancer, by administering effective amounts of an anti-VEGF antibody and one or more chemotherapeutic agents to a patient susceptible to, or diagnosed with, previously untreated ovarian cancer or recurrent ovarian cancer. A variety of chemotherapeutic agents may be used in the combined treatment methods of the invention. An exemplary and non-limiting list of chemotherapeutic agents contemplated is provided herein under "Definition", or described herein.

In one example, the invention features the use of a VEGF-specific antagonist with one or more chemotherapeutic agents (e.g., a cocktail) or any combination thereof. In certain embodiments, the chemotherapeutic agent is for example, taxane, paclitaxel, docetaxel, paclitaxel protein-bound particles (e.g., Abraxane®), platinum analogs, carboplatin, gemcitabine, or combinations thereof therapy. In one embodiment, the chemotherapeutic agents are carboplatin and pacilataxel or docetaxel. In another embodiment, the chemotherapeutic agents are carboplatin and gemcitabine. The combined administration includes simultaneous administration, using separate formulations or a single pharmaceutical formulation, and consecutive administration in either order, wherein preferably there is a time period while both (or all) active agents simultaneously exert their biological activities followed by maintenance therapy with a VEGF specific antagonist, e.g., as outlined in FIG. 1, FIG. 2, or FIG. 8 or FIG. 11. Preparation and dosing schedules for such chemotherapeutic agents may be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). The chemotherapeutic agent may precede, or follow administration of the VEGF-specific antagonist or may be given simultaneously therewith. In certain embodiments of the invention, the dosing schedules and amounts are as set forth in FIG. 1, FIG. 2 or FIG. 8 or FIG. 11.

In some other aspects, other therapeutic agents useful for combination tumor therapy with the antibody of the invention include antagonist of other factors that are involved in tumor growth, such as EGFR, ErbB2 (also known as Her2) ErbB3, ErbB4, or TNF. Sometimes, it may be beneficial to also administer one or more cytokines to the patient. In a one embodiment, the VEGF antibody is co-administered with a growth inhibitory agent. For example, the growth inhibitory agent may be administered first, followed by the VEGF antibody. However, simultaneous administration or administration of the VEGF antibody first is also contemplated. Suitable dosages for the growth inhibitory agent are those presently used and may be lowered due to the combined action (synergy) of the growth inhibitory agent and anti-VEGF antibody.

The formulation herein may also contain more than one active compound as necessary for the particular indication being treated, preferably those with complementary activities that do not adversely affect each other. For example, it may be desirable to further provide antibodies which bind to EGFR, VEGF (e.g. an antibody which binds a different epitope on VEGF), VEGFR, ErbB2 (e.g., Herceptin®) or another antibody used in oncology indications in the one formulation. Alternatively, or in addition, the composition may comprise a cytotoxic agent, cytokine, growth inhibitory agent and/or small molecule VEGFR antagonist. Such molecules are suitably present in combination in amounts that are effective for the purpose intended. In certain embodiments, VEGF antagonist (e.g., anti-VEGF antibody) is the treatment for ovarian cancer. In certain embodiments, VEGF antagonist (e.g., anti-VEGF antibody) is combined with carboplatin and paclitaxel followed by anti-VEGF maintenance therapy. In certain embodiments, VEGF antagonist (e.g., anti-VEGF antibody) is combined with cisplatin and paclitaxel followed by anti-VEGF maintenance therapy. In certain embodiments, VEGF antagonist (e.g., anti-VEGF antibody) is combined with carboplatin and docetaxel followed by anti-VEGF maintenance therapy. In certain embodiments, VEGF antagonist (e.g., anti-VEGF antibody) is combined with carboplatin and gemcitabine followed by anti-VEGF maintenance therapy.

In certain aspects, other therapeutic agents useful for combination cancer therapy with the antibody of the invention include other anti-angiogenic agents. Many anti-angiogenic agents have been identified and are known in the arts, including those listed by Carmeliet and Jain (2000). In one embodiment, the anti-VEGF antibody of the invention is used in combination with another VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, two or more anti-VEGF antibodies may be co-administered to the patient.

For the prevention or treatment of disease, the appropriate dosage of VEGF-specific antagonist will depend on the type of disease to be treated, as defined above, the severity and course of the disease, whether the VEGF-specific antagonist is administered for preventive or therapeutic purposes, previous therapy, the patient's clinical history and response to the VEGF-specific antagonist, and the discretion of the attending physician. The VEGF-specific antagonist is suitably administered to the patient at one time or over a series of treatments. In a combination therapy regimen, the VEGF-specific antagonist and the one or more anti-cancer therapeutic agent of the invention are administered in a therapeutically effective or synergistic amount. As used herein, a therapeutically effective amount is such that co-administration of a VEGF-specific antagonist and one or more other therapeutic agents, or administration of a composition of the invention, results in reduction or inhibition of the cancer as described above. A therapeutically synergistic amount is that amount of a VEGF-specific antagonist and one or more other therapeutic agents necessary to synergistically or significantly reduce or eliminate conditions or symptoms associated with a particular disease or to increase progression free survival.

The VEGF-specific antagonist and the one or more other therapeutic agents can be administered simultaneously or sequentially in an amount and for a time sufficient to reduce or eliminate the occurrence or recurrence of a tumor, a dormant tumor, or a micrometastases. The VEGF-specific antagonist can be administered as maintenance therapy to prevent or reduce the likelihood of recurrence of the tumor or increase progression free survival of the patient.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In addition to the above therapeutic regimes, the patient may be subjected to radiation therapy.

In certain embodiments, the administered VEGF antibody is an intact, naked antibody. However, the VEGF antibody may be conjugated with a cytotoxic agent. In certain embodiments, the conjugated antibody and/or antigen to which it is bound is/are internalized by the cell, resulting in increased therapeutic efficacy of the conjugate in killing the cancer cell to which it binds. In one embodiment, the cytotoxic agent targets or interferes with nucleic acid in the cancer cell. Examples of such cytotoxic agents include maytansinoids, calicheamicins, ribonucleases and DNA endonucleases.

The invention also features a method of instructing a human subject with ovarian cancer by providing instructions to receive treatment with an anti-VEGF antibody so as to increase the time for progression free survival, to decrease the subject's risk of cancer recurrence or to increase the subject's likelihood of survival. In some embodiments the method further comprises providing instructions to receive treatment with at least one chemotherapeutic agent followed by anti-VEGF maintenance therapy. In some embodiments the method further comprises providing instructions to receive treatment with two or more chemotherapeutic agents followed by anti-VEGF maintenance therapy. The treatment with the anti-VEGF antibody may be concurrent with the treatment with the chemotherapeutic agent(s). In certain embodiments the subject is treated as instructed by the method of instructing. Treatment of ovarian cancer by administration of an anti-VEGF antibody with or without chemotherapy may be continued until cancer recurrence or death. In certain embodiments of the invention, the patient is treated with at least 16 cycles of anti-VEGF therapy after concurrent therapy with chemotherapeutic agent(s). In other embodiments of the invention, the patient is treated with at least 12 cycles of anti-VEGF therapy after concurrent therapy with chemotherapeutic agent(s).

The invention further provides a promotional method, comprising promoting the administration of an anti-VEGF antibody for treatment of ovarian cancer in a human subject. In some embodiments the method further comprises promoting the administration of at least one chemotherapeutic agent followed by anti-VEGF maintenance therapy. In some embodiments the method further comprises promoting the administration of two or more chemotherapeutic agent followed by anti-VEGF maintenance therapy. Administration of the anti-VEGF antibody may be concurrent with administration of the chemotherapeutic agent(s). Promotion may be conducted by any means available. In some embodiments the promotion is by a package insert accompanying a commercial formulation of the anti-VEGF antibody. The promotion may also be by a package insert accompanying a commercial formulation of the chemotherapeutic agent(s). Promotion may be by written or oral communication to a physician or health care provider. In some embodiments the promotion is by a package insert where the package inset provides instructions to receive ovarian cancer therapy with anti-VEGF antibody. In a further embodiment, the package insert include some or all of the results under Example 1 or Example 2 or Example 3. In some embodiments the promotion is followed by the treatment of the subject with the anti-VEGF antibody with or without the chemotherapeutic agent(s).

The invention provides a business method, comprising marketing an anti-VEGF antibody for treatment of ovarian cancer in a human subject so as to increase the subject's time for progression free survival, to decrease the subject's likelihood of cancer recurrence or increase the subject's likelihood of survival. In some embodiments the method further comprises marketing a chemotherapeutic agent for use in combination with the anti-VEGF antibody followed by anti-VEGF maintenance therapy. In some embodiments the marketing is followed by treatment of the subject with the anti-VEGF antibody with or without the chemotherapeutic agent followed by anti-VEGF maintenance therapy. In some embodiments the method further comprises marketing two or more chemotherapeutic agents for use in combination with the anti-VEGF antibody followed by anti-VEGF maintenance therapy. In some embodiments the marketing is followed by treatment of the subject with the anti-VEGF antibody with or without the chemotherapeutic agents followed by anti-VEGF maintenance therapy.

Also provided is a business method, comprising marketing a chemotherapeutic agent in combination with an anti-VEGF antibody for treatment of ovarian cancer in a human subject so as to increase the subject's time for progression free survival, to decrease the subject's likelihood of cancer recurrence or increase the subject's likelihood of survival. In some embodiments the marketing is followed by treatment of the subject with the combination of the chemotherapeutic agent and the anti-VEGF antibody followed by anti-VEGF maintenance therapy. Also provided is a business method, comprising marketing two or more chemotherapeutic agents in combination with an anti-VEGF antibody followed by anti-VEGF maintenance therapy for treatment of ovarian cancer in a human subject so as to increase the subject's time for progression free survival, to decrease the subject's likelihood of cancer recurrence or increase the subject's likelihood of survival. In some embodiments the marketing is followed by treatment of the subject with the combination of the chemotherapeutic agents and the anti-VEGF antibody followed by anti-VEGF maintenance therapy.

IV Dosages, and Duration

The VEGF-specific antagonist composition will be formulated, dosed, and administered in a fashion consistent with good medical practice. Factors for consideration in this context include the particular disorder being treated, the particular subject being treated, the clinical condition of the individual patient, the cause of the disorder, the site of delivery of the agent, the method of administration, the scheduling of administration, and other factors known to medical practitioners. The "therapeutically effective amount" of the VEGF-specific antagonist to be administered will be governed by such considerations, and is the minimum amount necessary to prevent, ameliorate, or treat, or stabilize, the cancer; to increase the time until progression (duration of progression free survival) or to treat or prevent the occurrence or recurrence of a tumor, a dormant tumor, or a micrometastases. The VEGF-specific antagonist need not be, but is optionally, formulated with one or more agents currently used to prevent or treat cancer or a risk of developing a cancer. The effective amount of such other agents depends on the amount of VEGF-specific antagonist present in the formulation, the type of disorder or treatment, and other factors discussed above. These are generally used in the same dosages and with administration routes as used hereinbefore or about from 1 to 99% of the heretofore employed dosages.

Depending on the type and severity of the disease, about 1 μg/kg to 100 mg/kg (e.g., 0.1-20 mg/kg) of VEGF-specific antagonist is an initial candidate dosage for administration to the patient, whether, for example, by one or more separate administrations, or by continuous infusion. A typical daily dosage might range from about 1 μg/kg to about 100 mg/kg or more, depending on the factors mentioned above. Particularly desirable dosages include, for example, 5 mg/kg, 7.5 mg/kg, 10 mg/kg, and 15 mg/kg. For repeated administrations over several days or longer, depending on the condition, the treatment is sustained until the cancer is treated, as measured by the methods described above or known in the art. However, other dosage regimens may be useful. In one example, if the VEGF-specific antagonist is an antibody, the antibody of the invention is administered once every week, every two weeks, or every three weeks, at a dose range from about 5 mg/kg to about 15 mg/kg, including but not limited to 5 mg/kg, 7.5 mg/kg, 10 mg/kg or 15 mg/kg. The progress of the therapy of the invention is easily monitored by conventional techniques and assays. In other embodiments, such dosing regimen is used in combination with a chemotherapy regimen (including but not limited to one or more chemotherapeutic agent(s)) as the first line therapy for treating previously untreated ovarian cancer followed by maintenance therapy. In other embodiments, such dosing regimen is used in combination with a chemotherapy regimen (including but not limited to one or more chemotherapeutic agent(s)) as the second line therapy for treating recurrent ovarian cancer followed by maintenance therapy. Further information about suitable dosages is provided in the Examples below.

The duration of therapy will continue for as long as medically indicated or until a desired therapeutic effect (e.g., those described herein) is achieved. In certain embodiments, the VEGF-specific antagonist therapy is continued for 1 month, 2 months, 4 months, 6 months, 8 months, 10 months, 1 year, 2 years, 3 years, 4 years, 5 years, or for a period of years up to the lifetime of the subject. In certain embodiments, the anti-VEGF therapy is continued for at least 16 cycles after the concurrent anti-VEGF treatment with chemotherapeutic agents. In other embodiments, the anti-VEGF therapy is continued for at least 12 cycles after the concurrent anti-VEGF treatment with chemotherapeutic agents.

The VEGF-specific antagonists of the invention are administered to a subject, e.g., a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration is particularly desired if extensive side effects or toxicity is associated with VEGF antagonism. An ex vivo strategy can also be used for therapeutic applications. Ex vivo strategies involve transfecting or transducing cells obtained from the subject with a polynucleotide encoding a VEGF antagonist. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

For example, if the VEGF-specific antagonist is an antibody, the antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

In another example, the VEGF-specific antagonist compound is administered locally, e.g., by direct injections, when the disorder or location of the tumor permits, and the injections can be repeated periodically. The VEGF-specific antagonist can also be delivered systemically to the subject or directly to the tumor cells, e.g., to a tumor or a tumor bed following surgical excision of the tumor, in order to prevent or reduce local recurrence or metastasis, for example of a dormant tumor or micrometastases.

Alternatively, an inhibitory nucleic acid molecule or polynucleotide containing a nucleic acid sequence encoding a VEGF-specific antagonist can be delivered to the appropriate cells in the subject. In certain embodiments, the nucleic acid can be directed to the tumor itself.

The nucleic acid can be introduced into the cells by any means appropriate for the vector employed. Many such methods are well known in the art (Sambrook et al., supra, and Watson et al., *Recombinant DNA*, Chapter 12, 2d edition, Scientific American Books, 1992). Examples of methods of gene delivery include liposome mediated transfection, electroporation, calcium phosphate/DEAE dextran methods, gene gun, and microinjection.

V. Pharmaceutical Formulations

Therapeutic formulations of the antibodies used in accordance with the invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Preferred lyophilized anti-VEGF antibody formulations are described in WO 97/04801, expressly incorporated herein be reference.

Optionally, the formulation contains a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

Typically, bevacizumab is supplied for therapeutic uses in 100 mg and 400 mg preservative-free, single-use vials to deliver 4 ml or 16 ml of bevacizumab (25 mg/ml). The 100 mg product is formulated in 240 mg α, α-trehalose dehydrate, 23.2 mg sodium phosphate (monobasic, monohydrate), 4.8 mg sodium phosphate (dibasic, anhydrous), 1.6 mg polysorbate 20, and Water for Injection, USP. The 400 mg product is formulated in 960 mg α,α-trehalose dehydrate, 92.8 mg sodium phosphate (monobasic, monohydrate), 19.2 mg sodium phosphate (dibasic, anhydrous), 6.4 mg polysorbate 20, and Water for Injection, USP. See also the label for bevacizumab.

The formulation herein may also contain more than one active compound as necessary for the particular indication being treated, preferably those with complementary activities that do not adversely affect each other. For example, it may be desirable to further provide antibodies which bind to EGFR, VEGF (e.g. an antibody which binds a different epitope on VEGF), VEGFR, or ErbB2 (e.g., Herceptin®) in the one formulation. Alternatively, or in addition, the composition may comprise a cytotoxic agent, cytokine, growth inhibitory agent and/or small molecule VEGFR antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations to be used for in vivo administration should be sterile. This is readily accomplished by filtration through sterile filtration membranes.

VI Efficacy of the Treatment

The main advantage of the treatment of the invention is the ability of producing marked anti-cancer effects in a human patient without causing significant toxicities or adverse effects, so that the patient benefited from the treatment overall. The efficacy of the treatment of the invention can be measured by various endpoints commonly used in evaluating cancer treatments, including but not limited to, tumor regression, tumor weight or size shrinkage, time to progression, duration of survival, progression free survival, overall response rate, duration of response, and quality of life. Because the anti-angiogenic agents of the invention target the tumor vasculature and not necessarily the neoplastic cells themselves, they represent a unique class of anticancer drugs, and therefore unique measures and definitions of clinical responses to drugs may be employed. For example, tumor shrinkage of greater than 50% in a 2-dimensional analysis is the standard cut-off for declaring a response. However, the anti-VEGF antibody of the invention may cause inhibition of metastatic spread without shrinkage of the primary tumor, or may simply exert a tumouristatic effect. Accordingly, optionally other approaches to determining efficacy of an anti-angiogenic therapy are employed, including for example, measurement of plasma or urinary markers of angiogenesis and measurement of response through radiological imaging.

In another embodiment, the invention provides methods for increasing progression free survival of a human patient susceptible to or diagnosed with a cancer. Time to disease progression is defined as the time from administration of the drug until disease progression or death. In a preferred embodiment, the combination treatment of the invention using anti-VEGF antibody and one or more chemotherapeutic agents followed by anti-VEGF maintenance therapy significantly increases progression free survival by at least about 1 month, 2 months, 2.3 months, 2.9 months, 3.0 months, 3.8 months, preferably by about 1 to about 6.1 months, when compared to a treatment without anti-VEGF antibody maintenance therapy. In one embodiment, the PFS median in months (95% CI) is increased 3.8 months (0.717 (0.625, 0.824) with one-sided p-value (log rank) of <0.001)) in the patients treated with bevacizumab and taxane therapy (e.g., docetaxel or paclitaxel) and carboplatin followed by anti-VEGF maintenance therapy compared to control. In another embodiment, the difference in median PFS in months (95% CI) between patients receiving paclitaxel and carboplatin alone versus paclitaxel, carboplatin and anti-VEGF antibody followed by anti-VEGF maintenance therapy is 2.3 months with HR=0.79 and p-value (Log-Rank Test) of 0.0010.

VII Antibody Production (i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Various methods for making monoclonal antibodies herein are available in the art. For example, the monoclonal antibodies may be made using the hybridoma method first described by Kohler et al., *Nature,* 256:495 (1975), or by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications.* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice,* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature,* 348: 552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., Nature, 332:323-327 (1988); Verhoeyen et al., Science, 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Humanized anti-VEGF antibodies and affinity matured variants thereof are described in, for example, U.S. Pat. No. 6,884,879 issued Feb. 26, 2005.

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992).

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275). Human monoclonal anti-VEGF antibodies are described in U.S. Pat. No. 5,730,977, issued Mar. 24, 1998.

(iv) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(v) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry,* second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human VEGF. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues). In one embodiment, the antibody has 307/434 mutations.

Engineered antibodies with three or more (preferably four) functional antigen binding sites are also contemplated (US Appln No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

(vi) Immunoconjugates

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugate antibodies. Examples include $^{212}Bi$, $^{131}I$, $^{131}In$, $^{90}Y$ and $^{186}Re$.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(vii) Immunoliposomes

The antibody disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl Acad. Sci. USA,* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the invention can be conjugated to the liposomes as described in Martin et al. *J. Biol. Chem.* 257: 286-288

(1982) via a disulfide interchange reaction. A chemotherapeutic agent (such as Doxorubicin) is optionally contained within the liposome. See Gabizon et al. *J. National Cancer Inst.*81(19)1484 (1989)

VIII. Articles of Manufacture and Kits

In another embodiment of the invention, an article of manufacture containing materials useful for the treatment of the disorders described above is provided. The article of manufacture comprises a container, a label and a package insert. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-VEGF antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, and syringes. In addition, the article of manufacture comprises a package inserts with instructions for use, including for example instructing the user of the composition to administer the anti-VEGF antibody composition and a chemotherapeutic agent to the patient, e.g., taxane, paclitaxel, docetaxel, paclitaxel protein-bound particles (e.g., Abraxane®), platinum analogue, carboplatin, gemcitabine, or combinations thereof, followed by anti-VEGF maintenance therapy. The package insert may optionally contain some or all of the results found in Example 1 or Example 2 or Example 3.

The VEGF-specific antagonist can be packaged alone or in combination with other anti-cancer therapeutic compounds as a kit. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. In certain embodiments, the instructions comprises instructions for use, including for example instructing the user of the composition to administer the anti-VEGF antibody composition and a chemotherapeutic agent to the patient, e.g., taxane, paclitaxel, docetaxel, paclitaxel protein-bound particles (e.g., Abraxane®), platinum analogue, carboplatinm, gemcitabine, or combinations thereof followed by anti-VEGF maintenance therapy. The instructions may optionally contain some or all of the results found in Example 1 or Example 2 or Example 3. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Deposit of Materials

The following hybridoma cell line has been deposited under the provisions of the Budapest Treaty with the American Type Culture Collection (ATCC), Manassas, Va., USA:

| Antibody Designation | ATCC No. | Deposit Date |
|---|---|---|
| A4.6.1 | ATCC HB-10709 | Mar. 29, 1991 |

The following examples are intended merely to illustrate the practice of the invention and are not provided by way of limitation. The disclosures of all patent and scientific literatures cited herein are expressly incorporated in their entirety by reference.

EXAMPLES

Example 1

A Phase III Trial of Carboplatin and Paclitaxel Plus Placebo Versus Carboplatin and Paclitaxel Plus Concurrent Bevacizumab Followed by Placebo, Versus Carboplatin and Paclitaxel Plus Concurrent and Extended Bevacizumab, in Women with Newly Diagnosed, Previously Untreated, Stage III (Sub Optimally and Macroscopic Optimally Debulked) or IV, Epithelial Ovarian, Primary Peritoneal or Fallopian Tube Cancer Results are presented from a phase III randomized study to evaluate new treatment programs for patients with International Federation of Gynecologic Oncology (FIGO) stages III and IV, epithelial ovarian, peritoneal primary or fallopian tube cancer. Primary Objectives include to determine if the addition of 5 concurrent cycles of bevacizumab to 6 cycles of standard therapy (carboplatin and paclitaxel) [Arm II] increases the duration of progression-free survival (PFS) when compared to 6 cycles of standard therapy alone [Arm I] in women with newly diagnosed stage III (with any gross residual disease) and stage IV, epithelial ovarian, peritoneal primary or fallopian tube cancer; and, to determine if the addition of 5 concurrent cycles of bevacizumab plus extended bevacizumab for 16 cycles beyond the 6 cycles of standard therapy (carboplatin and paclitaxel) [Arm III] increases progression-free survival when compared to 6 cycles of standard therapy [Arm I] in women with newly diagnosed stage III (with any gross residual disease) and stage IV, epithelial ovarian, peritoneal primary or fallopian tube cancer.

GOG-0182-ICONS was a 5-arm randomized clinical trial comparing standard therapy (carboplatin and paclitaxel) with four investigational arms incorporating gemcitabine, topotecan and liposomal doxorubicin, either in combination or in sequence with paclitaxel and carboplatin. Major ovarian cancer clinical trials groups throughout the world participated in this study. This international collaboration provided a unique opportunity to accrue large numbers of patients in a timely manner which facilitated the simultaneous evaluation of multiple agents in a prospective randomized trial. With international participation, accrual exceeded 1,200 patients per year, and the trial reached its targeted accrual goal within four years of activation.

While the results of GOG-0182-ICON5 helped establish optimum chemotherapy for previously untreated patients with advanced ovarian and peritoneal primary cancer, the next generation of clinical trials will explore the impact of molecular targeted therapies in conjunction with chemotherapy. In particular, growth factor signal transduction inhibitors and anti-angiogenic agents as single agents and in combination with chemotherapy drugs are currently undergoing trials in women with these tumors. Many of these agents have been shown to have cytostatic effects and have shown synergy with chemotherapy in experimental models of human cancer. In this phase III trial, the impact on outcome of active biologic agents in combination with standard chemotherapeutic therapy plus or minus extended single agent administration, compared with standard chemotherapeutic therapy alone, in patients with advanced disease was evaluated.

Bevacizumab is a recombinant humanized version of a murine anti-human VEGF monoclonal antibody, named rhuMAb VEGF. Bevacizumab has been advanced into clinical development for use as a single agent to induce tumor growth inhibition in patients with solid tumors and for use in combination with cytotoxic chemotherapy to delay the time to disease progression in patients with metastatic solid tumors. See, e.g., Presta L G, et al. *Humanization of an anti-vascular endothelial growth factor monoclonal antibody for the therapy of solid tumors and other disorders. Cancer Res* 57:4593-9, 1997. The results of two single agent trials of bevacizumab for patients with recurrent epithelial ovarian and peritoneal primary cancer have been published. See, e.g., Burger R A, et al., *Phase II trial of bevacizumab in persistent or recurrent epithelial ovarian cancer or primary peritoneal cancer: a Gynecologic Oncology Group study. J Clin Oncol* 25(33):5165-5171, 2007; and, Cannistra S A, et al., *Phase II Study of Bevacizumab in Patients with Platinum Resistant Ovarian Cancer or Primary Peritoneal Serous Cancer. J Clin Oncol* 25(33):5180-86, 2007. GOG (GOG-0170-D) utilized two co-primary efficacy endpoints: clinical response by NCI RECIST criteria and proportion surviving progression-free for at least 6 months. 62 participants received bevacizumab at 15 mg/kg every 21 days until clinical or radiographic evidence of disease progression or development of unacceptable toxicity. The primary disease characteristics were typical of patients with recurrent ovarian cancer, and approximately 43% of patients were considered primarily platinum resistant. A 21% response rate was observed, and 40% were progression-free for at least 6 months, with a median PFS 4.7 months, compared with 1.8 months for a historical control based on previous negative phase II trials of cytotoxic agents in populations with similar clinical characteristics. Genentech AVF 2949 examined patients with a higher risk profile in terms of the potential for disease progression and adverse events, allowing only patients considered either primarily or secondarily platinum resistant and having received 2 or 3 previous cytotoxic regimens. These differences in eligibility ultimately translated into a higher level of platinum resistance, a greater number of prior regimens and a slightly worse performance status profile in the AVF population. Forty four patients were treated at the same dose and schedule for bevacizumab as used in GOG 170-D. Seven (16%) responses were documented, and 12 (27%) were progression-free for at least 6 months.

In this study two experimental arms were selected to compare with standard cytotoxic chemotherapy with paclitaxel and carboplatin: one incorporating 5 cycles of bevacizumab (concurrent bevacizumab) and the other with bevacizumab for an additional 16 cycles after completion of chemotherapy with paclitaxel and carboplatin (extended bevacizumab). Administration and doses are indicated in FIGS. 1 and 2. Calvert Formula for Carboplatin (AUC) Dosing:

Total dose(mg)=target *AUC*(in mg/mL/minute)*[*GFR* (in mL/minute)+25].

The statistical design for the primary endpoint the study was based on 90% power to detect PFS hazard ratio (HR) ≤0.77 (median PFS shift: 14.0 months (historical)→18.2 months. The primary analysis compared investigator-assessed PFS for each bevacizumab arm verses control ((analysis 1→by RECIST (see, e.g, Therasse et al., *J Natl. Cancer Inst.*, 92:205-16, 2000), global clinical deterioration, or CA-125; or by analysis 2→RECIST or global clinical deterioration, censoring CA-125). The baseline clinical characteristics of the patients are found in Table 1. The baseline surgical-pathologic characteristics of the patients are found in Table 2.

Eligible Patients: Patients with a histologic diagnosis of epithelial ovarian cancer, peritoneal primary carcinoma or fallopian tube cancer; FIGO stage III with any gross (macroscopic or palpable) residual disease or FIGO stage IV, defined surgically at the completion of initial abdominal surgery and with appropriate tissue available for histologic evaluation. The minimum surgery required was an abdominal surgery providing tissue for histologic evaluation and establishing and documenting the primary site and stage, as well as a maximal effort at tumor debulking If additional surgery was performed, it should have been in accordance with appropriate surgery for ovarian or peritoneal carcinoma described in the GOG Surgical Procedures Manual (https://www.gog.fc-cc.edu/manuals/pdf/surgman.pdf). However, the surgeon is not required to have performed all of the items contained in this section of the GOG Surgical Procedures Manual. Those patients with stage III cancer in which the largest maximal diameter of any residual tumor implant at the completion of this initial surgery is no greater than 1 cm will be defined as "optimal;" all others will be defined as "suboptimal." Measurable disease on post-operative imaging studies is not required for eligibility.

Patients with the following histologic epithelial cell types are eligible: Serous adenocarcinoma, endometrioid adenocarcinoma, mucinous adenocarcinoma, undifferentiated carcinoma, clear cell adenocarcinoma, mixed epithelial carcinoma, transitional cell carcinoma, malignant Brenner's Tumor, or adenocarcinoma not otherwise specified (N.O.S.). However, the histologic features of the tumor must be compatible with a primary Müllerian epithelial adenocarcinoma. Patients may have co-existing fallopian tube carcinoma in-situ so long as the primary origin of invasive tumor is ovarian, peritoneal or fallopian tube.

Patients must have adequate:

(1) Bone marrow function: Absolute neutrophil count (ANC) greater than or equal to 1,500/µl, equivalent to Common Toxicity Criteria for Adverse Events v3.0 (CTCAE) Grade1. This ANC cannot have been induced or supported by granulocyte colony stimulating factors.

(2) Platelets greater than or equal to 100,000/µl. (CTCAE Grade 0-1).

(3) Renal function: Creatinine≤1.5× institutional upper limit normal (ULN), CTCAE Grade 1.

(4) Hepatic function:
 (a) Bilirubin less than or equal to 1.5×ULN (CTCAE Grade 1).
 (b) SGOT and alkaline phosphatase less than or equal to 2.5×ULN (CTCAE Grade 1).
 c) Neurologic function: Neuropathy (sensory and motor) less than or equal to CTCAE Grade 1.

(5) Blood coagulation parameters: PT such that international normalized ratio (INR) is ≤1.5 (or an in-range INR, usually between 2 and 3, if a patient is on a stable dose of therapeutic warfarin for management of venous thrombosis including pulmonary thrombo-embolus) and a PTT<1.2 times the upper limit of normal.

(6) Patients with a GOG Performance Status of 0, 1, or 2.

(7) Patients must be entered between 1 and 12 weeks after initial surgery performed for the combined purpose of diagnosis, staging and cytoreduction.
(8) Patients with measurable and non-measurable disease are eligible. Patients may or may not have cancer-related symptoms.
(9) Patients who have met the pre-entry requirements specified in Section 7.0.
(10) An approved informed consent and authorization permitting release of personal health information must be signed by the patient or guardian.
(11) Patients in this trial may receive ovarian estrogen+/−progestin replacement therapy as indicated at the lowest effective dose(s) for control of menopausal symptoms at any time, but not progestins for management of anorexia while on protocol directed therapy or prior to disease progression.

Ineligible Patients: Patients with a current diagnosis of borderline epithelial ovarian tumor (formerly "tumors of low malignant potential") or recurrent invasive epithelial ovarian, primary peritoneal or fallopian tube cancer treated with surgery only (such as patients with stage Ia or Ib low grade epithelial ovarian or fallopian tube cancers) are not eligible. Patients with a prior diagnosis of a borderline tumor that was surgically resected and who subsequently develop an unrelated, new invasive epithelial ovarian, peritoneal primary or fallopian tube cancer are eligible, provided that they have not received prior chemotherapy for any ovarian tumor.

Patients who have received prior radiotherapy to any portion of the abdominal cavity or pelvis are excluded. Prior radiation for localized cancer of the breast, head and neck, or skin is permitted, provided that it was completed more than three years prior to registration, and the patient remains free of recurrent or metastatic disease.

Patients who have received prior chemotherapy for any abdominal or pelvic tumor including neo-adjuvant chemotherapy for their ovarian, primary peritoneal or fallopian tube cancer are excluded. Patients may have received prior adjuvant chemotherapy for localized breast cancer, provided that it was completed more than three years prior to registration, and that the patient remains free of recurrent or metastatic disease.

Patients who have received any targeted therapy (including but not limited to vaccines, antibodies, tyrosine kinase inhibitors) or hormonal therapy for management of their epithelial ovarian or peritoneal primary cancer.

Patients with synchronous primary endometrial cancer, or a past history of primary endometrial cancer, are excluded, unless all of the following conditions are met: Stage not greater than I-B; no more than superficial myometrial invasion, without vascular or lymphatic invasion; no poorly differentiated subtypes, including papillary serous, clear cell or other FIGO Grade 3 lesions.

With the exception of non-melanoma skin cancer and other specific malignancies as noted above, patients with other invasive malignancies who had (or have) any evidence of the other cancer present within the last five years or whose previous cancer treatment contraindicates this protocol therapy are excluded.

Patients with acute hepatitis or active infection that requires parenteral antibiotics.

Patients with serious non-healing wound, ulcer, or bone fracture. This includes history of abdominal fistula, gastrointestinal perforation or intra-abdominal abscess within 28 days. Patients with granulating incisions healing by secondary intention with no evidence of fascial dehiscence or infection are eligible but require weekly wound examinations.

Patients with active bleeding or pathologic conditions that carry high risk of bleeding, such as known bleeding disorder, coagulopathy, or tumor involving major vessels.

Patients with history or evidence upon physical examination of CNS disease, including primary brain tumor, seizures not controlled with standard medical therapy, any brain metastases, or history of cerebrovascular accident (CVA, stroke), transient ischemic attack (TIA) or subarachnoid hemorrhage within six months of the first date of treatment on this study.

Patients with clinically significant cardiovascular disease. This includes: Uncontrolled hypertension, defined as systolic>150 mm Hg or diastolic>90 mm Hg.; Myocardial infarction or unstable angina<6 months prior to registration; New York Heart Association (NYHA) Grade II or greater congestive heart failure; Serious cardiac arrhythmia requiring medication. This does not include asymptomatic, atrial fibrillation with controlled ventricular rate; CTCAE Grade 2 or greater peripheral vascular disease (at least brief (<24 hrs) episodes of ischemia managed non-surgically and without permanent deficit); History of CVA within six months.

Patients with known hypersensitivity to Chinese hamster ovary cell products or other recombinant human or humanized antibodies.

Patients with clinically significant proteinuria. Urine protein should be screened by urine protein-creatinine ratio (UPCR). The UPCR has been found to correlate directly with the amount of protein excreted in a 24 hour urine collection. See, e.g., Ginsberg J M, et al., *Use of single voided urine samples to estimate quantitative proteinuria. N Engl J Med* 309:1543-6, 1983; Rodby R A, et al., *The urine protein to creatinine ratio as a predictor of 24-hour urine protein excretion in type 1 diabetic patients with nephropathy. The Collaborative Study Group. Am J Kidney Dis* 26:904-9, 1995; Schwab S J, et al., *Quantitation of proteinuria by the use of protein-to-creatinine ratios in single urine samples. Arch Intern Med* 147:943-4, 1987; Steinhauslin F, & Wauters J P. *Quantitation of proteinuria in kidney transplant patients: accuracy of the urinary protein/creatinine ratio. Clin Nephrol* 43:110-5, 1995; Wilson D M, & Anderson R L. *Protein-osmolality ratio for the quantitative assessment of proteinuria from a random urinalysis sample. Am J Clin Pathol* 100:419-24, 1993; and, Zelmanovitz T, et al., *Proteinuria is still useful for the screening and diagnosis of overt diabetic nephropathy. Diabetes Care* 21:1076-9, 1998. Specifically, a UPCR of 1.0 is equivalent to 1.0 gram of protein in a 24 hour urine collection. Patients must have a UPCR<1.0 to allow participation in the study.

Patients with or with anticipation of invasive procedures as defined below: Major surgical procedure, open biopsy or significant traumatic injury within 28 days prior to the first date of bevacizumab/placebo therapy (cycle 2). Major surgical procedure anticipated during the course of the study. This includes, but is not limited to abdominal surgery (laparotomy or laparoscopy) prior to disease progression, such as colostomy or enterostomy reversal, interval or secondary cytoreductive surgery, or second look surgery. Core biopsy, within 7 days prior to the first date of bevacizumab/placebo therapy (cycle 2).

Patients with GOG Performance Grade of 3 or 4.
Patients who are pregnant or nursing.
Patients under the age of 18.
Patients who have received prior therapy with any anti-VEGF drug, including bevacizumab.
Patients with clinical symptoms or signs of gastrointestinal obstruction and who require parenteral hydration and/or nutrition.

Patients with other medical history or condition that in the opinion of the doctor, would preclude study participation.

Response and progression will be evaluated in this study using the international criteria proposed by the Response Evaluation Criteria in Solid Tumors (RECIST) Committee. See, e.g., Therasse P, et al. *New guidelines to evaluate the response to treatment in solid tumors. European Organization for Research and Treatment of Cancer, National Cancer Institute of the United States, National Cancer Institute of Canada. J Natl Cancer Inst* 92:205-16, 2000. Changes in only the largest diameter (unidimensional measurement) of the tumor lesions are used in the RECIST criteria.

CA-125 as a Biologic Marker of Progressive Disease: Serum levels of CA-125, a tumor-associated glycoprotein antigen, are elevated in 80% of patients with epithelial ovarian cancer. See, e.g., Bast et al., *N. Engl. J. Med.* 309:88307, 1983. CA-125 has been monitored, often on a frequent basis, to verify response to therapy, presence of residual disease, and as early evidence of recurrence. However, CA-125, is not entirely tumor specific, and can be elevated in a variety of benign conditions, such as endometriosis, uterine fibroids, and pelvic inflammation; this is particularly true in pre-menopausal women. In addition, levels of CA-125 can be discordant with tumor response, both as false-positive and false-negative trends; the influence of biologic agents on these inaccuracies is unclear. Nonetheless, it has been standard practice for patients and physicians interpret a progressive rise in CA-125 post-therapy as evidence of recurrent or progressive disease, and will make therapeutic decisions based on CA-125. The current randomized trial will employ a conservative formula to define progressive disease based on serial elevation of CA-125, (in addition to other standard definitions in the management of solid tumors), but only following completion of initial chemotherapy. See, e.g., Guppy et al., *Oncologists*, 7:437043, 2002; Rustin et al., *J. Clin. Oncol.* 19:4054-7, 2001; Rustin, *J. Clin. Oncol.*, 21:187-93, 2003; Rustin et al., *Clin. Cancer Res.* 10:3919-26, 2004; and, Rustin et al., *J Natl. Cancer Inst.*, 96:487-8, 2004. In one example, progress based upon serum CA-125 can be determined only during the period following completion of cytotoxic chemotherapy, if one of the three conditions are met: 1) patients with elevated CA-125 pretreatment and normalization of CA-125 must show evidence of CA-125 greater than or equal to two times the upper normal limited on two occasions at least one week apart; or 2) patients with elevated CA-125 pretreatment, which never normalizes must show evidence of CA-125 greater than or equal to two times the nadir value on two occasions at least one week apart; or 3) patients with CA-125 in the normal range pretreatment must show evidence of CA-125 greater than or equal to two times the upper normal limit on two occasions at least one week apart.

Results

Figures 6, 7:
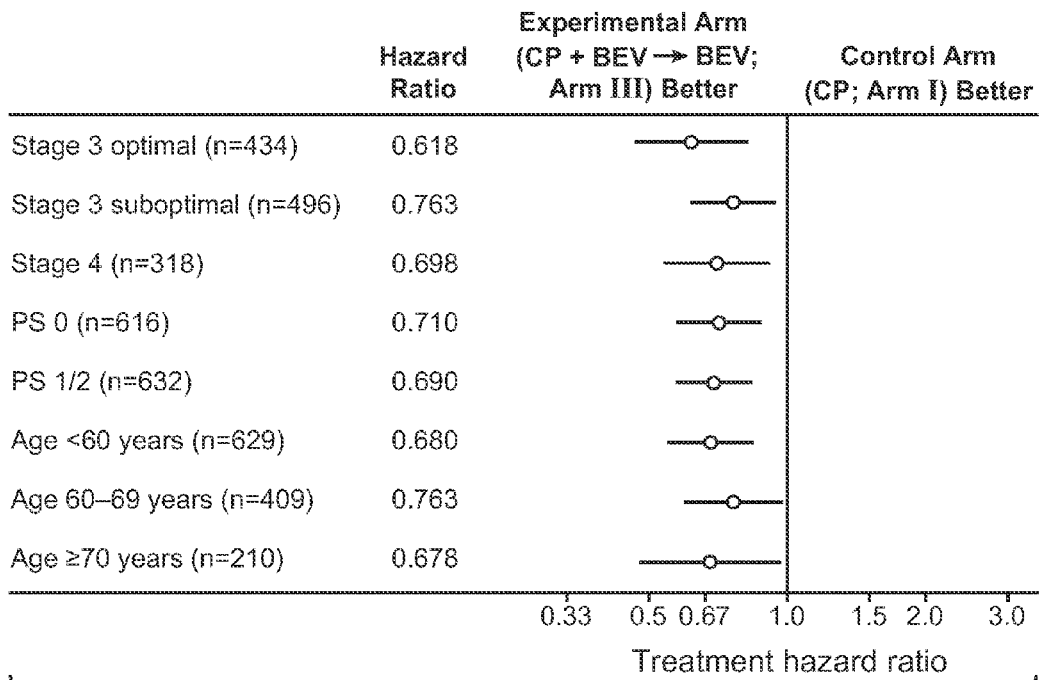
FIG. 6 depicts PFS values for Arm I and Arm III of the trial depicted in FIG. 2 and the ramifications of using CA-125 marker as determinant of progression.
FIG. 7 depicts a subgroup analyses of patients in Arm III verses Arm I of the trial depicted in FIG. 2.

The results of the study demonstrate that bevacizumab is effective for first line ovarian cancer when combined with chemotherapy and continued as maintenance therapy. This combination was effective at increasing PFS. Preliminary assessment of safety identified bevacizumab related adverse events (AEs) noted in previous studies. The primary analysis of PFS demonstrated a progression-free survival (months) median of 10.3 (in arm one of FIG. 2) compared to 14.1 months in arm three of FIG. 2. The HR (95% CI) was 0.908 (0.795, 1.04) with a one-sided p-value (log-rank of 0.08) in arm I of FIG. 2 compared to 0.717 (0.625, 0.824) with one-sided p-value (log-rank) of <0.001 in arm III of FIG. 2. See FIG. 5. The difference was statistically significant. The treatment regimen was generally well tolerated and adverse events (including GI perforation) were similar to previous bevacizumab studies. See FIG. 3 and FIG. 4. This is the first anti-angiogenic therapy to demonstrate benefit in this population. FIG. 6 illustrates the ramification of using CA-125 as a determinant of progression. CA-125 is an antigenic determinant on a high-molecular weight glycoprotein recognized by a monoclonal antibody (OC-125), which is produced using an ovarian cancer cell line as an immunogen. CA 125 has been evaluated as a serum marker for monitoring patients with epithelial ovarian carcinoma and other cancers. See, e.g., references *Gyn Oncol* 38:373, 1990; *Gyn Oncol* 38:181, 1990; *Amer J Ob Gyn* 160:667, 1989; *Amer J Ob Gyn* 159:873, 1988; *Amer J Ob Gyn* 159:341, 1988; *Ob Gyn* 72:159, 1988; and, *Gyn Oncol* 36:299, 1990 and descriptions herein. FIG. 7 illustrates subgroup analyses of Arm I verses Arm III.

TABLE 1

Baseline Clinical Characteristics

| Characteristic | Arm I<br>CP<br>(n = 625) | Arm II<br>CP + BEV<br>(n = 625) | Arm III<br>CP + BEV → BEV<br>(n = 623) |
|---|---|---|---|
| Median age, years (range) | 60 (25-86) | 60 (24-88) | 60 (22-89) |
| Race, n (%) | | | |
| Non-Hispanic white | 526 (84) | 519 (83) | 521 (84) |
| Asian | 41 (7) | 37 (6) | 39 (6) |
| Non-Hispanic black | 25 (4) | 28 (5) | 27 (4) |
| Hispanic | 21 (3) | 28 (5) | 25 (4) |
| Other, specified | 8 (1) | 5 (<1) | 4 (<1) |
| GOG PS, n (%) | | | |
| 0 | 311 (50) | 315 (50) | 305 (49) |
| 1 | 272 (44) | 270 (43) | 267 (43) |
| 2 | 42 (7) | 40 (6) | 51 (8) |

TABLE 2

Baseline Surgical-Pathologic Characteristics

| Characteristic, n (%) | Arm I<br>CP<br>(n = 625) | Arm II<br>CP + BEV<br>(n = 625) | Arm III<br>CP + BEV → BEV<br>(n = 623) |
|---|---|---|---|
| Stage/residual size | | | |
| III optimal (macroscopic) | 218 (35) | 205 (33) | 216 (35) |
| III suboptimal | 254 (41) | 256 (41) | 242 (39) |
| IV | 153 (25) | 164 (26) | 165 (27) |
| Histology | | | |
| Serous | 543 (87) | 523 (84) | 525 (84) |
| Endometrioid | 20 (3) | 15 (2) | 25 (4) |
| Clear cell | 11 (2) | 23 (4) | 18 (3) |
| Mucinous | 8 (1) | 5 (<1) | 8 (1) |
| Tumor grade | | | |
| 3a | 412 (66) | 435 (70) | 430 (69) |
| 2 | 94 (15) | 77 (12) | 92 (15) |
| 1 | 33 (5) | 28 (4) | 16 (3) |
| Not specified/pending | 86 (14) | 85 (14) | 85 (14) |

Example 2

A Randomized, Two-Arm, Multi-Center Gynaecologic Cancer Intergroup Trial of Adding Bevacizumab to Standard Chemotherapy (Carboplatin and Paclitaxel) in Patients with Epithelial Ovarian Cancer Results are presented from a phase III randomized study (ICON7) to evaluate the safety and efficacy of adding bevacizumab to standard chemotherapy with carboplatin and paclitaxel. The primary endpoint was to determine whether the addition of bevacizumab to standard chemotherapy improves progression free survival (PFS) when compared to standard chemotherapy alone in women with newly diagnosed, histologically confirmed, high risk International Federation of Gynaecology and Obstetrics (FIGO) stage I and IIa (Grade 3 or clear cell carcinoma only) and FIGO stage IIb-IV (all grades and all histological types) epithelial ovarian, fallopian tube or primary peritoneal cancer, who have undergone initial surgery (either debulking cytoreductive surgery or a biopsy if the patient has FIGO stage IV disease) and who would not be considered for cytoreductive surgery prior to disease progression. Secondary endpoints included overall survival (OS), response rate, duration of response, biological progression free interval (defined by increasing CA 125 or $PFI_{BIO}$), safety and quality of life. ICON7 was a 2-arm randomized clinical trial comparing standard therapy (carboplatin and paclitaxel) with one investigational arm incorporating bevacizumab in combination with paclitaxel and carboplatin (see FIG. 8). A total of 1528 eligible women participated in the trial.

Bevacizumab is a recombinant humanized version of a murine anti-human VEGF monoclonal antibody, named rhuMAb VEGF. Bevacizumab has been advanced into clinical development for use as a single agent to induce tumor growth inhibition in patients with solid tumors and for use in combination with cytotoxic chemotherapy to delay the time to disease progression in patients with metastatic solid tumors. See, e.g., Presta L G, et al. *Humanization of an anti-vascular endothelial growth factor monoclonal antibody for the therapy of solid tumors and other disorders. Cancer Res* 57:4593-9, 1997.

Patient Selection

ICON7 included patients with newly diagnosed, histologically confirmed, high risk FIGO stage I and IIa (Grade 3 or clear cell carcinoma only) and FIGO stage IIb-IV (all grades and all histological types) epithelial ovarian, fallopian tube or primary peritoneal cancer, who have undergone initial surgery (either debulking cytoreductive surgery or a biopsy if the patient has FIGO stage IV disease) and who will not be considered for cytoreductive surgery prior to disease progression. Patients with measurable and non-measurable disease are eligible. Patients were considered eligible for enrollment in this trial if they fulfilled all the inclusion criteria and none of the exclusion criteria as described below:

Patient Inclusion Criteria:
- Females aged ≥18 years
- Histologically confirmed, with core biopsy from a disease site as minimum requirement, (cytology alone was insufficient for diagnosis)
  - Epithelial Ovarian cancer
  - Primary peritoneal carcinoma (must be of the papillary-serous histological type) or
  - Fallopian tube carcinoma
  - AND meeting the criteria in Table 3

Patients with clear cell carcinoma of any stage were eligible due to the poorer prognosis associated with this subtype. Patients with previous early stage epithelial ovarian or fallopian tube carcinoma treated with surgery alone were eligible at the time of diagnosis of abdomino-pelvic recurrence as long as no further interval cytoreductive therapy was planned prior to disease progression.

For the purposes of this trial, clear cell carcinoma was defined as either ≥50% clear cell elements present or reported as clear cell carcinoma by the local pathologist.

TABLE 3

Histological Eligibility Criteria

| FIGO Stage | Eligible Grade 1 | Grade 2 | Grade 3 |
|---|---|---|---|
| Ia | No$^E$ | No$^E$ | Yes |
| Ib | No$^E$ | No$^E$ | Yes |
| Ic | No$^E$ | No$^E$ | Yes |
| IIa | No$^E$ | No$^E$ | Yes |
| IIb | Yes | Yes | Yes |
| IIc | Yes | Yes | Yes |
| III | Yes | Yes | Yes |
| IV | Yes | Yes | Yes |

Grade refers to 1 (well differentiated), 2 (moderately differentiated) and 3 (poorly differentiated)
$^E$= Except patients with clear cell carcinoma who are eligible regardless of FIGO stage

- Patients should have already undergone surgical debulking, by a surgeon experienced in the management of ovarian cancer, with the aim of maximal surgical cytoreduction according to the GCIG Conference Consensus Statement. There must be no planned surgical debulking prior to disease progression.
- Patients with stage III and IV disease in whom initial surgical debulking was not appropriate were still be eligible providing
  - the patient had a histological diagnosis and
  - debulking surgery prior to disease progression was not forseen
- Patients should have been able to commence systemic therapy within eight weeks of cytoreductive surgery. If the patient was randomised to the research arm then the first dose of bevacizumab must be omitted if the investigator decides to start chemotherapy within 4 weeks of surgery.
- If a patient had two operations, for example an initial operation to remove what was thought to be a benign cyst and then a second gynae-oncological operation to formally stage and maximally debulk the ovarian tumour, then the second operation date was documented as the date of surgery; the first systemic treatment started within eight weeks of this date. The date of diagnosis was recorded as the date of the initial operation where ovarian cancer was diagnosed.
- ECOG performance status (PS) 0-2
- Life expectancy>12 weeks
- Adequate bone marrow function (all parameters were checked/calculated on post-operative bloods) (within 28 days prior to randomisation)
  - Absolute Neutrophil Count (ANC)≥1.5×10$^9$/l
  - Platelets (PLT)≥100×10$^9$/l
  - Haemoglobin (Hb)≥9 g/dl (can be post-transfusion)
- Adequate coagulation parameters (all parameters were checked/calculated on post-operative bloods) (within 28 days prior to randomisation)
  - Activated ProThrombin Time (APTT)≤1.5×ULN; or,
  - International Normalised Ratio (INR)≤1.5 (measurement of INR was mandatory if patient was receiving warfarin treatment)

Adequate liver function (all parameters were checked/calculated on post-operative bloods) (within 28 days prior to randomisation)
  Serum bilirubin (BR)≤1.5×ULN
  Serum transaminases≤2.5×ULN
Urine dipstick for proteinuria<2+. If urine dipstick is ≥2+, 24 hour urine must demonstrate≤1 g of protein in 24 hours
Adequate renal function defined as a serum creatinine≤2.0 mg/dl or ≤177 μmol/l Patient Exclusion Criteria:
Non-epithelial ovarian cancer, including malignant mixed Mullerian tumours
Borderline tumours (tumours of low malignant potential)
Planned intraperitoneal cytotoxic chemotherapy
Prior systemic anti-cancer therapy for ovarian cancer (for example chemotherapy, monoclonal antibody therapy, tyrosine kinase inhibitor therapy or hormonal therapy)
Surgery (including open biopsy) within 4 weeks prior to anticipated first dose of bevacizumab (allowing for the fact that bevacizumab can be omitted from the first cycle of chemotherapy)
Any planned surgery during the 58 week period from the start of study treatment (54 weeks of treatment plus 4 additional weeks to allow for bevacizumab clearance)
Uncontrolled hypertension (blood pressure measurements were recorded in patients after 5 minutes of rest, and in the sitting position) (Sustained elevation of BP>150/100 mmHg despite anti-hypertensive therapy)
Any previous radiotherapy to the abdomen or pelvis
Significant traumatic injury during 4 weeks preceding the potential first dose of bevacizumab
History or clinical suspicion of brain metastases or spinal cord compression. CT/MRI of the brain is mandatory (within 4 weeks prior to randomisation) in case of suspected brain metastases. Spinal MRI is mandatory (within 4 weeks prior to randomisation) in case of suspected spinal cord compression
History or evidence upon neurological examination of central nervous system (CNS) disease, unless adequately treated with standard medical therapy e.g. uncontrolled seizures
Previous Cerebro-Vascular Accident (CVA), Transient Ischaemic Attack (TIA) or Sub-Arachnoid Haemorrhage (SAH) within six months prior to randomisation
Fertile woman of childbearing potential not willing to use adequate contraception (oral contraceptives, intrauterine device or barrier method of contraception in conjunction with spermicidal jelly or surgically sterile) for the study duration and at least six months afterwards
Pregnant or lactating women
Previous exposure to mouse CA 125 antibody
Treatment with any other investigational agent, or participation in another clinical trial within 30 days prior to entering this trial
Malignancies other than ovarian cancer within 5 years prior to randomisation, except for adequately treated carcinoma in situ of the cervix and/or basal cell skin cancer and/or early endometrial carcinoma as specified below. Patients may have received previous adjuvant chemotherapy for other malignancies e.g. breast or colorectal carcinoma if diagnosed over 5 years ago with no evidence of subsequent recurrence
Patients with synchronous primary endometrial carcinoma, or a past history of primary endometrial carcinoma, were excluded unless ALL of the following criteria for describing the endometrial carcinoma were met
  Stage≤Ib
  No more than superficial myometrial invasion
  No lymphovascular invasion
  Not poorly differentiated (i.e. not Grade 3 or papillary serous or clear cell)
Known hypersensitivity to bevacizumab and its excipients or chemotherapy (including cremophor)
Non healing wound, ulcer or bone fracture. Patients with granulating incisions healing by secondary intention with no evidence of facial dehiscence or infection were eligible but required three weekly wound examinations
History or evidence of thrombotic or hemorrhagic disorders
Clinically significant cardiovascular disease, including
  Myocardial infarction or unstable angina within 6 months of randomisation
  New York Heart Association (NYHA)≥Grade 2 Congestive Heart Failure (CHF)
  Poorly controlled cardiac arrhythmia despite medication (patients with rate-controlled atrial fibrillation were eligible)
  Grade≥3 peripheral vascular disease (i.e. symptomatic and interfering with activities of daily living [ADL] requiring repair or revision)
Current or recent (within 10 days prior to cycle 1 treatment) chronic use of aspirin>325 mg/day (Low-dose aspirin (<325 mg/day) did not appear to increase the risk of grade 3-4 bleeding when used with bevacizumab plus chemotherapy, therefore the use of prophylactic low-dose aspirin in patients who are at risk of an arterial thromboembolic event was not prohibited in this trial protocol)
Current or recent (within 10 days prior to cycle 1 treatment) use of full-dose oral or parenteral anticoagulants or thrombolytic agent for therapeutic purposes (except for line patency, in which case INR must be maintained below 1.5)
Pre-existing sensory or motor neuropathy≥Grade 2
Evidence of any other disease, metabolic dysfunction, physical examination finding or laboratory finding giving reasonable suspicion of a disease or condition that contra-indicates the use of an investigational drug or puts the patient at high risk for treatment-related complications Tumor assessments, either by CT or MRI scan, with measurements using the RECIST criteria, were performed after three and six cycles of chemotherapy, and at around nine months and 12 months in the first year, or after cycle 12 and cycle 18 of treatment for patients on the research arm. In the second and third year of the trial tumour assessments were repeated every six months and thereafter as clinically indicated. These scans were performed irrespective of whether the patient has been optimally or sub-optimally debulked, and irrespective of whether there is measurable disease, or not, on the baseline scan.

Patients were clinically assessed and CA 125 measured at the start of every chemotherapy cycle and then six weekly during the first year of the trial. In the second and third year of the trial patients were assessed and CA 125 measured every three months. In the fourth and fifth year patients were clinically assessed and CA 125 measured every six months. Thereafter assessments were yearly. Progression based on CA 125 criteria alone were verified with a CT scan. If this was negative then it was repeated at the time of suspected clinical progression.

After evidence of protocol defined disease progression, patients were followed for survival and subsequent treatment for ovarian cancer every six months during the first five years of their follow up in the trial and yearly thereafter.

Regular physical examination and routine blood tests were performed during treatment to monitor patient safety. Quality of life (QoL) were assessed using the EORTC QLQ C-30+ OV-28 and EQ-5D questionnaires at the start of every chemotherapy cycle, every six weeks until the end of the first year and then every three months until treatment for progression commenced, or to the end of year two. An additional QoL form was completed by all patients still alive three years after randomisation. Adverse events and medical resource use were documented during the study treatment and follow-up period.

Results

Figure 10:
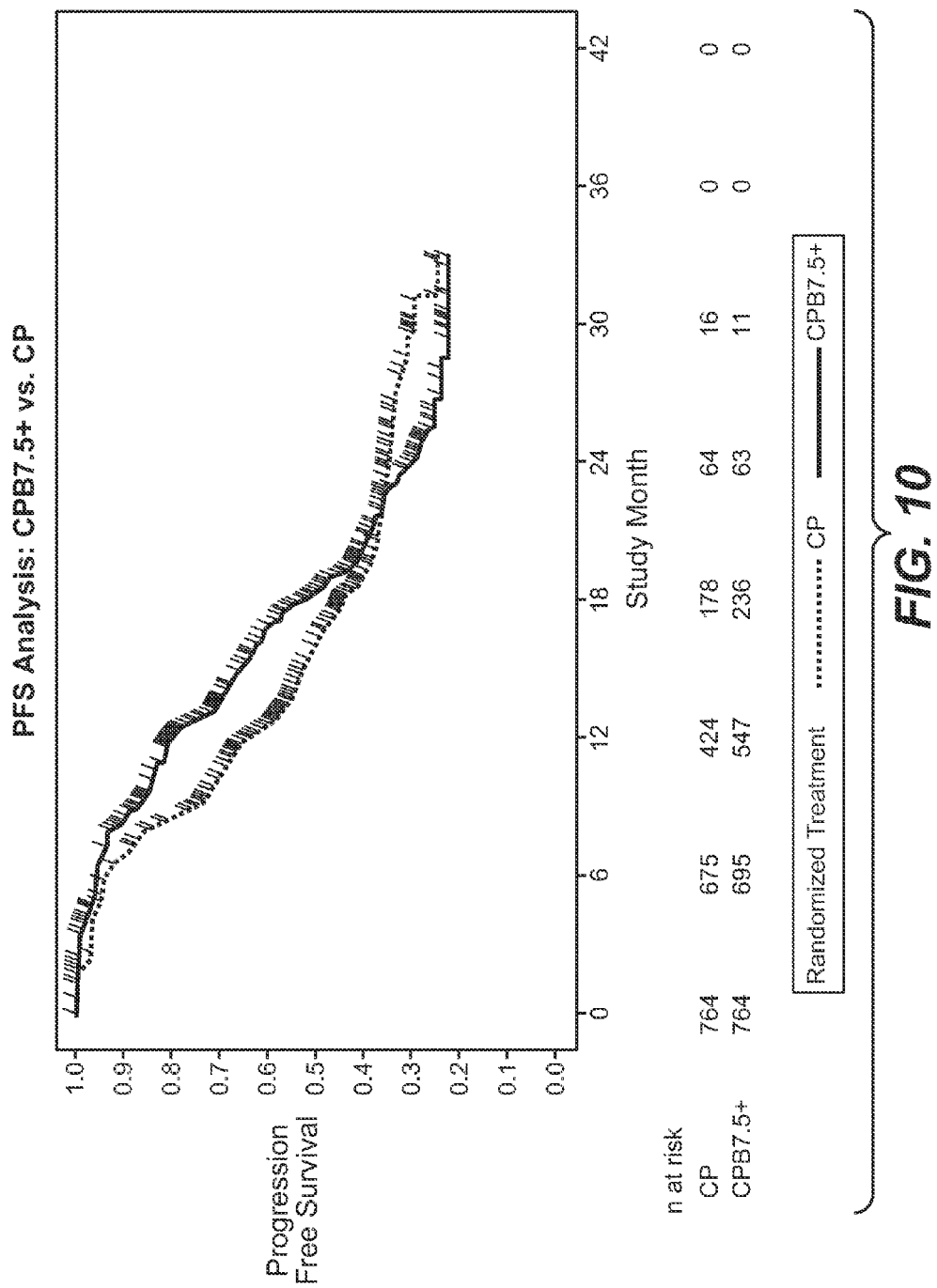
FIG. 10 depicts a graph of the PFS results from the trial depicted in FIG. 8. "CP" corresponds to Arm A in FIG. 8. "CPB7.5+" corresponds to Arm B in FIG. 8.

The results of the study demonstrate that bevacizumab is effective for first line ovarian cancer when combined with chemotherapy and continued as maintenance therapy for a total duration of 12 months. This combination was effective at increasing progression-free survival (PFS). The primary analysis of PFS demonstrated a PFS median of 16.0 months in the chemotherapy arm (CP) compared to 18.3 months in the chemotherapy plus bevacizumab arm (CPB7.5+) with a p-value (Log-Rank Test) of 0.0010. The hazard ratio (HR) (95% CI) was 0.79 (0.68; 0.91). The difference was significant. The PFS analysis is summarized in FIGS. 9 and 10.

The baseline characteristics were as follows:

TABLE 4

Baseline Characteristics - Demographics

|  | CP (N = 764) | CPB7.5+ (N = 764) |
|---|---|---|
| Age in years: Mean (SD) | 56.7 (10.6) | 56.5 (10.4) |
| Race: White (%) | 737 (96%) | 730 (96%) |
| Performance status (ECOG) | | |
| 0 (%) | 333 (44%) | 307 (41%) |
| 1 (%) | 375 (49%) | 391 (52%) |
| 2 (%) | 54 (7%) | 55 (7%) |

TABLE 5

Baseline Characteristics - History of Ovarian Cancer

|  | CP (N = 764) | CPB7.5+ (N = 764) |
|---|---|---|
| Origin of Cancer | | |
| Ovary (Epithelial) (%) | 667 (87%) | 673 (88%) |
| Fallopian Tube (%) | 29 (4%) | 27 (4%) |
| Primary Peritoneal (%) | 56 (7%) | 50 (7%) |
| Multiple Locations (%) | 12 (2%) | 14 (2%) |
| FIGO staging | | |
| I (%) | 65 (8%) | 54 (7%) |
| II (%) | 80 (11%) | 83 (11%) |
| III (%) | 522 (68%) | 523 (68%) |
| IV (%) | 97 (13%) | 104 (14%) |

TABLE 6

Baseline Characteristics - History of Ovarian Cancer

|  | CP (N = 764) | CPB7.5+ (N = 764) |
|---|---|---|
| Degree of Differentiation | | |
| Grade 1 (%) | 56 (7%) | 41 (5%) |
| Grade 2 (%) | 142 (19%) | 175 (23%) |
| Grade 3 (%) | 556 (74%) | 538 (71%) |

TABLE 6-continued

Baseline Characteristics - History of Ovarian Cancer

|  | CP (N = 764) | CPB7.5+ (N = 764) |
|---|---|---|
| Histological Subtype | | |
| Serous (%) | 529 (69%) | 525 (69%) |
| Mucinous (%) | 15 (2%) | 19 (2%) |
| Endometroid (%) | 57 (7%) | 60 (8%) |
| Clear cell (%) | 60 (8%) | 67 (9%) |
| Other (%) | 55 (7%) | 53 (7%) |
| Mixed (%) | 48 (6%) | 40 (5%) |

TABLE 7

Baseline Characteristics - Surgery of Ovarian Cancer

|  | CP (N = 764) | CPB7.5+ (N = 764) |
|---|---|---|
| Debulking surgery performed: Yes (%) | 747 (98%) | 751 (98%) |
| Debulking surgery outcome: Optimal (%) | 552 (74%) | 559 (74%) |
| Time between surgery and first trial treatment [days]: Mean (SD) | 35.6 (10.2) | 35.9 (9.9) |

Preliminary assessment of adverse events for bevacizumab were consistent with previous studies.

TABLE 8

Overview of Adverse Events (AEs)

|  | CP (N = 763) | CPB7.5+ (N = 746) |
|---|---|---|
| Pts w. Serious AE | 154 (20.2%) | 279 (37.4%) |
| Pts w. Grade 3/4/5 AE | 385 (50.5%) | 479 (64.2%) |
| Pts who Disc. Any Treatment | 98 (12.8%) | 293 (39.3%) |
| Pts who Disc. Any Treatment due to AE | 68 (8.9%) | 162 (21.7%) |
| All Deaths | 131 (17.2%) | 107 (14.3%) |
| All Related Deaths | 1 (0.1%) | 5 (0.7%) |
| Deaths not due to Progression | 16 (2.1%) | 19 (2.5%) |

Example 3

A Phase III, Multicenter, Randomized, Blinded, Placebo-Controlled Trial of Carboplatin and Gemcitabine Plus Bevacizumab in Patients with Platinum-Sensitive Recurrent Ovary, Primary Peritoneal, or Fallopian Tube Carcinoma Epithelial ovarian carcinoma (EOC) and its histological and clinical equivalents, primary peritoneal carcinoma (PPC) and fallopian tube carcinoma, occur at an incidence of approximately 25,000 cases per year in the United States and result in approximately 14,000 deaths per annum. Because the disease tends to be asymptomatic in early stages, the majority of patients will present initially with advanced (Stage III or IV) disease. Despite the sensitivity of EOC, PPC, and fallopian tube carcinoma to a number of chemotherapeutic agents, particularly the taxanes and platinum compounds, only 20%-30% of patients who present with Stage III or IV disease will be alive at 5 years. Patients with platinum-sensitive recurrent cancer (defined as recurrence of disease more than 6 months from the completion of a platinum based chemotherapy regimen) have higher initial response rates to chemotherapy; however, these patients are not considered curable. Recently, the U.S. Food and Drug Administration (FDA) approved gemcitabine chemotherapy in combination with carboplatin for relapsed platinum sensitive disease. Carboplatin and gemcitabine resulted in a statistically significant progression-free survival (PFS) compared with carboplatin alone in patients with platinum sensitive disease. See, e.g., Pfisterer, Plante M, Vergote I, et al. *Gemcitabine plus Carboplatin compared with carboplatin in patients with platinum-sensitive recurrent ovarian cancer: an intergroup trial of the AGO-OVAR, the NCIC CTG, and the EORTC GCG. J. Clin Oncol,* 2006;24:4699707.

Angiogenesis appears to be an important factor in both the development and subsequent progression of EOC. Yoneda and colleagues (1998) demonstrated in a xenograft model of EOC that tumor growth rates were directly proportional to vascular density and that the development of malignant ascites, a feature associated with poor outcome in EOC, was associated with the expression of vascular endothelial growth factor (VEGF). See, e.g., Yoneda J, Kuniyasu H, Crispens M A, et al. *Expression of angiogenesis-related genes and progression of human ovarian carcinomas in nude mice. J Natl Cancer Inst.* 1998 Mar. 18; 90:44754. Other studies have demonstrated the association of VEGF expression in EOC with microvascular density. Moreover, studies have shown that the expression density of CD31 (a marker of vascular endothelium) by immunohistochemistry in EOC inversely correlates with survival.

This example describes a placebo-controlled, randomized, multicenter Phase III study evaluating the efficacy and safety of bevacizumab (15 mg/kg, Day 1, every 21 days), administered in combination with carboplatin (area under the curve [AUC] 4, Day 1, every 21 days) with gemcitabine (1000 mg/m2, Day 1 and Day 8, every 21 days) in women with platinum sensitive recurrent epithelial ovarian, primary peritoneal, or fallopian tube carcinoma. About 480 patients were enrolled over a period of approximately 2.5 years. Patients were randomized in either carboplatin and gemcitabine with placebo versus carboplatin and gemcitabine with bevacizumab. In addition, at randomization, patients were stratified by platinum-sensitive disease (recurrence 6-12 months from last platinum based treatment versus recurrence>12 months from last platinum-based treatment) and cytoreductive surgery for recurrent epithelial ovarian, primary peritoneal, or fallopian tube carcinomas (surgery was performed vs. was not performed).

| 484 women randomized 1:1 to one of two treatment arms: | | | |
|---|---|---|---|
| | | Phase A (cycles 1-6; cycle = three weeks) | Phase B (until disease progression = three weeks) |
| Patients | Arm 1 | Chemotherapy + placebo | Placebo |
| | Arm 2 | Avastin + chemotherapy | Avastin |

The study consisted of the two arms shown below. See also FIG. 11.

Arm 1: Carboplatin (AUC 4 IV) and gemcitabine (1000 mg/m2) chemotherapies (6 cycles up to 20 cycles) followed by placebo Arm 2: Avastin (15 mg/kg for 6 cycles up p 10 cycles) in combination with carboplatin and gemcitabine chemotherapies (6 cycles up to 10 cycles) followed by the continued use of Avastin (15 mg/kg) alone until disease progression The carboplatin dose was calculated to reach a target AUC of concentration x time according to the Calvert formula with use of an estimated glomerular filtration rate (GFR); e.g., for the purposes here, the GFR is considered to be equivalent to the creatinine clearance.

Calvert Formula for Carboplatin (AUC) Dosing $$\text{total dose(mg)} = \text{target } AUC(\text{in mg/mL/minute}) \times [GFR(\text{in mL/minute}) 25]$$

Creatinine clearance can be calculated according to institutional guidelines.

Patient Selection

Patients with epithelial carcinoma of the ovary, PPC, or fallopian tube carcinoma that has recurred>6 months since platinum-based chemotherapy (first recurrence) will be eligible for this study. Additional specific inclusion and exclusion criteria are listed below.

Patient Inclusion Criteria:

Patients must meet the following criteria to be eligible for study entry:

Signed Informed Consent Form

Age≥18 years

Histologically documented ovarian, primary peritoneal, or fallopian tube carcinoma that has recurred>6 months after platinum based chemotherapy The patient must have recurrent epithelial ovarian, primary peritoneal, or fallopian tube carcinoma. This must be the first recurrence of epithelial ovarian, primary peritoneal, or fallopian tube carcinoma.

Examples of eligible histological cell types include: serous adenocarcinoma, endometrioid adenocarcinoma, mucinous adenocarcinoma, undifferentiated carcinoma, clear cell adenocarcinoma, transitional cell carcinoma, malignant Brenner's Tumor, or adenocarcinoma not otherwise specified No prior chemotherapy in the recurrent setting Measurable disease according to modified RECIST with at least one lesion that can be accurately measured in at least one dimension (longest dimension recorded)

Each measurable lesion must be 20 mm when measured by conventional techniques, CT and magnetic resonance imaging (MRI), or 10 mm when measured by spiral CT.

Greater than 28 days from and recovered from prior radiation therapy or surgery

ECOG performance status 0 or 1

Use of an effective means of contraception (for women of childbearing potential)

Ability to comply with study and follow up procedures

Patient Exclusion Criteria

Patients who meet any of the following criteria will be excluded from study entry.

Disease-Specific Exclusions

Prior chemotherapy treatment for recurrent ovarian, primary peritoneal, or fallopian tube carcinoma: Hormonal therapy (i.e., progesterones, estrogens, anti estrogens, aromatase inhibitors) will not be considered a prior chemotherapy regimen. Concomitant anti-neoplastic anti-hormonal therapy (including tamoxifen, aromatase inhibitors, etc.) is not allowed for patients participating in study treatment. Low-dose (physiologic) estrogen hormone-replacement therapy (HRT) may be given.

History of abdominal fistula, gastrointestinal perforation, or intra abdominal abscess Patients with clinical symptoms or signs of GI obstruction or who require parenteral hydration, parenteral nutrition, or tube feeding Patients with evidence of abdominal free air not explained by paracentesis or recent surgical procedure General Medical Exclusions
  Life expectancy of <12 weeks
  Current, recent (within 4 weeks of Day 1, Cycle 1), or planned participation in an experimental drug study
  Screening clinical laboratory values
    Granulocyte count<1500/µL
    Platelet count<100,000/µL
    Hemoglobin<8.5 g/dL (hemoglobin may be supported by transfusion or erythropoietin or other approved hematopoietic growth factors)
    Serum bilirubin>2.0× upper limits of normal (ULN)
    Alkaline phosphatase, aspartate transaminase (AST), and/or alanine transaminase (ALT)>2.5×ULN (AST, ALT>5×ULN for patients with liver metastasis)
    Serum creatinine≥1.6
    International normalized ratio (INR)>1.5 and/or activated partial thromboplastin time (aPTT)>1.5× ULN (except for patients receiving anticoagulation therapy)
    For patients on full-dose warfarin, in-range INR (usually between 2 and 3) and a PTT<1.2 times the ULN
  History of other malignancies within 5 years of Day 1, Cycle 1, except for tumors with a negligible risk for metastasis or death, such as adequately controlled basal-cell carcinoma or squamous cell carcinoma of the skin or carcinoma in situ of the cervix
  Any other diseases, metabolic dysfunction, physical examination finding, or clinical laboratory finding giving reasonable suspicion of a disease or condition that contraindicates the use of an investigational drug or that may affect the interpretation of the results or render the patient at high risk for treatment complications Bevacizumab-Specific Exclusions
  History of systemic bevacizumab (Avastin®) or other VEGF or VEGF receptor targeted agent use
  Inadequately controlled hypertension (defined as systolic blood pressure>150 mmHg and/or diastolic blood pressure>100 mmHg on antihypertensive medications)
  Prior history of hypertensive crisis or hypertensive encephalopathy
  New York Heart Association Class II or greater CHF
  History of myocardial infarction or unstable angina within 6 months prior to Day 1, Cycle 1 (day of the first bevacizumab/placebo infusion)
  History of stroke or TIA within 6 months prior to study enrollment
  Known CNS disease except for treated brain metastasis
    Treated brain metastases are defined as having no evidence of progression or hemorrhage after treatment and no ongoing requirement for dexamethasone, as ascertained by clinical examination and brain imaging (MRI or CT) during the screening period. These metastases must not be located in the brainstem, midbrain, pons, medulla, or leptomeninges. Treatment for brain metastases may include whole brain radiotherapy (WBRT), radiosurgery (Gamma Knife, LINAC, or equivalent) or a combination as deemed appropriate by the treating physician. Patients with CNS metastases treated by neurosurgical resection or brain biopsy performed within 3 months prior to Day 1 will be excluded.
  History of significant vascular disease (e.g., aortic aneurysm, aortic dissection)
  Recent peripheral arterial thrombosis within 6 months prior to Day 1, Cycle 1
  History of hemoptysis (≥½ teaspoon of bright red blood per episode) within 1 month prior to Day 1, Cycle 1
  Evidence of bleeding diathesis or significant coagulopathy (in the absence of therapeutic anticoagulation)
  Major surgical procedure, open biopsy, or significant traumatic injury within 28 days prior to Day 1, Cycle 1 or anticipation of need for major surgical procedure during the course of the study
  Core biopsy or other minor surgical procedure, excluding placement of a vascular access device, within 7 days prior to Day 1, Cycle 1
  Serious, non-healing wound; active ulcer; or untreated bone fracture
  Proteinuria at screening, as demonstrated by a UPCR of ≥1.0 at screening
  Known hypersensitivity to any component of bevacizumab
  Pregnancy (positive pregnancy test) or lactation
  Patients of childbearing potential must use an effective means of contraception.

This study, OCEANS, enrolled a different patient population from example 1 (GOG 0218) and example 2 (ICON7); women with previously treated, platinum-sensitive ovarian cancer were eligible for this trial. Women with ovarian cancer may have receive a platinum-based chemotherapy as the first line of treatment. The time between receiving the last dose of platinum-based chemotherapy and disease coming back (recurrence) is used to help determine the choice of chemotherapy used in the next line of treatment. Women have "platinum-sensitive" ovarian cancer if the disease comes back more than six months after completing initial platinum-based chemotherapy. Ovarian cancer is considered "platinum-resistant" if it comes back within six months of completing initial platinum-based chemotherapy.

Results

This phase III study of bevacizumab plus chemotherapy in women with ovarian cancer met its primary endpoint. The object of the study was to evaluate the efficacy and safety of adding bevacizumab in to standard chemotherapy followed by extended use of bevacizumab alone until disease progression, compared to chemotherapy alone, in previously treated women with ovarian cancer. The study showed that bevacizumab plus chemotherapy, followed by continued use of bevacizumab alone until disease progression, increased the time women with previously treated (recurrent), platinum-sensitive ovarian cancer lived without the disease worsening (progression-free survival or PFS), compared to chemotherapy alone. PFS is defined as the time from randomization to disease progression as determined by the investigator or death due to any cause, whichever occurs first. The primary endpoint of PFS was assessed by the study investigators. Measurable disease was investigator assessed using modified RECIST (Therasse et al. 2000), e.g., every 9 weeks throughout the course of the study. See, e.g., Therasse P, Arbuck S G, Eisenhauser E A, et al. *New guidelines to evaluate the response to treatment in solid tumors. J Natl Cancer Inst* 2000;92:205-1. Secondary endpoints included overall survival (OS), response rate, duration of response and safety. No new safety findings were observed and adverse events were consistent with those observed in previous pivotal trials of bevacizumab.

What is claimed is:

1. A method of treating a patient diagnosed with recurrent platinum-sensitive advanced epithelial ovarian, fallopian tube or primary peritoneal cancer, comprising subjecting the patient to a treatment regimen combining carboplatin and gemcitabine with the concurrent administration of 15 mg/kg of an anti-VEGF antibody having a heavy chain variable region comprising the following amino acid sequence:

```
                                            (SEQ ID NO. 1)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSS
``` and a light chain variable region comprising the following amino acid sequence:

```
                                            (SEQ ID NO. 2)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR
``` followed by anti-VEGF antibody maintenance therapy, and wherein the treatment regimen effectively extends the progression free survival of the patient.

2. The method of claim 1, wherein said anti-VEGF antibody binds the same epitope as the monoclonal anti-VEGF antibody A4.6.1 produced by hybridoma ATCC HB 10709.

3. The method of claim 1, wherein the anti-VEGF antibody is a humanized antibody.

4. The method of claim 3, wherein the anti-VEGF antibody is a humanized A4.6.1 antibody or fragment thereof.

5. The method of claim 3, wherein the anti-VEGF antibody is bevacizumab.

6. The method of claim 1, wherein the carboplatin is administered at an area under the concentration-time curve (AUC) of 4.

7. The method of claim 1, wherein the gemcitabine is administered at 1000 mg/m$^2$.

8. The method of claim 1, wherein the anti-VEGF antibody maintenance is administered at 15 mg/kg.

9. The method claim 1, wherein the progression free survival of the patient is extended by at least about 2.3 months or more compared to another patient not treated with anti-VEGF antibody.

10. The method of claim 1, wherein the patient is diagnosed with Stage III or Stage IV ovarian cancer.

* * * * *

UNITED STATES PATENT AND TRADEMARK OFFICE
CERTIFICATE OF CORRECTION

| | | |
|---|---|---|
| PATENT NO. | : 8,778,340 B2 | Page 1 of 1 |
| APPLICATION NO. | : 13/032532 | |
| DATED | : July 15, 2014 | |
| INVENTOR(S) | : Dupont et al. | |

It is certified that error appears in the above-identified patent and that said Letters Patent is hereby corrected as shown below:

Title Page, Item (75) Inventor is corrected to read:

--Jakob Dupont, Hillsborough, CA
 Cornelia Irl, Basel (CH)
 Amreen Husain, San Mateo, CA
 Mika A. Sovak, Burlingame, CA
 Jing Yi, South San Francisco, CA
 Hoa Nguyen, South San Francisco, CA--.

Signed and Sealed this
Sixth Day of January, 2015

Michelle K. Lee
*Deputy Director of the United States Patent and Trademark Office*